(12) United States Patent
Pascolo

(10) Patent No.: US 9,771,594 B2
(45) Date of Patent: Sep. 26, 2017

(54) PHARMACEUTICAL COMPOSITION CONSISTING OF RNA HAVING ALKALI METAL AS COUNTER ION AND FORMULATED WITH DICATIONS

(71) Applicant: Steve Pascolo, Zurich (CH)

(72) Inventor: Steve Pascolo, Zurich (CH)

(73) Assignee: spRNA GmbH (CH)

( * ) Notice: Subject to any disclaimer, the term of this patent is extended or adjusted under 35 U.S.C. 154(b) by 0 days.

(21) Appl. No.: 13/919,663

(22) Filed: Jun. 17, 2013

(65) Prior Publication Data

US 2014/0004154 A1  Jan. 2, 2014

Related U.S. Application Data

(63) Continuation of application No. PCT/EP2011/073151, filed on Dec. 16, 2011.

(30) Foreign Application Priority Data

Dec. 16, 2010  (EP) .................................... 10195493

(51) Int. Cl.
| | | |
|---|---|---|
| *C12N 15/117* | (2010.01) | |
| *A61K 9/00* | (2006.01) | |
| *A61K 47/02* | (2006.01) | |
| *C12N 15/88* | (2006.01) | |
| *C12N 15/11* | (2006.01) | |
| *C12N 15/113* | (2010.01) | |

(52) U.S. Cl.
CPC .......... *C12N 15/117* (2013.01); *A61K 9/0019* (2013.01); *A61K 47/02* (2013.01); *C12N 15/11* (2013.01); *C12N 15/113* (2013.01); *C12N 15/88* (2013.01)

(58) Field of Classification Search
None
See application file for complete search history.

(56) References Cited

U.S. PATENT DOCUMENTS

| 2004/0229358 A1* | 11/2004 | Lewis et al. .................. 435/455 |
| 2008/0267873 A1 | 10/2008 | Hoerr et al. |
| 2010/0144846 A1* | 6/2010 | Jurk ..................... C12N 15/117 514/44 R |

FOREIGN PATENT DOCUMENTS

EP  1083232 A1  3/2001

OTHER PUBLICATIONS

Protocol Online—siRna (RNA Oligo) Annealing Protocol [online]. [Retrieved on Feb. 23, 2015]. Retrieved from the Internet: <http://www.protocol-online.org>.*
Pollard, Jack. "Purificationof Oligonucleotides Using Denaturing Polyacrylamide Gel Electrophoresis." (1998) Retrieved from the internet on Nov. 16, 2015. Retrieved from <http://molbio.mgh.harvard.edu/szostakweb/protocols/denaturepage.>.*
International Search Report & Written Opinion of the International Searching Authority Application No. PCT/EP2011/073151 Completed: Jul. 6, 2012; Mailing Date: Aug. 2, 2012 12 pages.
Probst, et al.; "Spontaneous Cellular Uptake of Exogenous Messenger RNA in Vivo is Nucleic Acid-Specific, Saturable and Ion Dependent"; Gene Therapy (2007) 14, [ages 1175-1180.

* cited by examiner

*Primary Examiner* — Jennifer McDonald
(74) *Attorney, Agent, or Firm* — St Onge Steward Johnston and Reens LLC

(57) ABSTRACT

A biologically active RNA-alkali metal-dication formulation, a pharmaceutical composition containing the complexes, and methods of producing the same. The formulation is particularly useful to introduce RNA and an attached cargo into cells allowing its biological intracellular activities: e.g. immunostimulation (immunomodulation), RNA interference or gene expression.

29 Claims, 11 Drawing Sheets

The biological activity of RNA requires that sodium is the counter ion

Desalted RNA is strongly biologically active

RNA is biologically active when diluted in Calcium-containing solutions

RNA is biologically active when diluted in Calcium-containing solutions

RNA sequence requirements

RNA sequence requirements

Fig. 4

Examples of structures of RNAs according to the invention

A

5' AGUGUUAUCUUGUAUGGGGGG 3'   SEQ ID NO: 1

B

Sense strand     5' NNNNNNNNNNNNNNNNNNNNNGGGGGG 3'
Antisens strand  5' NNNNNNNNNNNNNNNNNNNNNN 3'      SEQ ID NO: 16

C

5' Cap-UTR5'-Startcodon-codingsequence-stopcodon-UTR3'-AAAAA(A)AAAAAGGGGGG 3'

SEQ ID NO: 17

Formulated RNA is stable at room temperature

Formulated RNA is stable few minutes in the presence of RNases

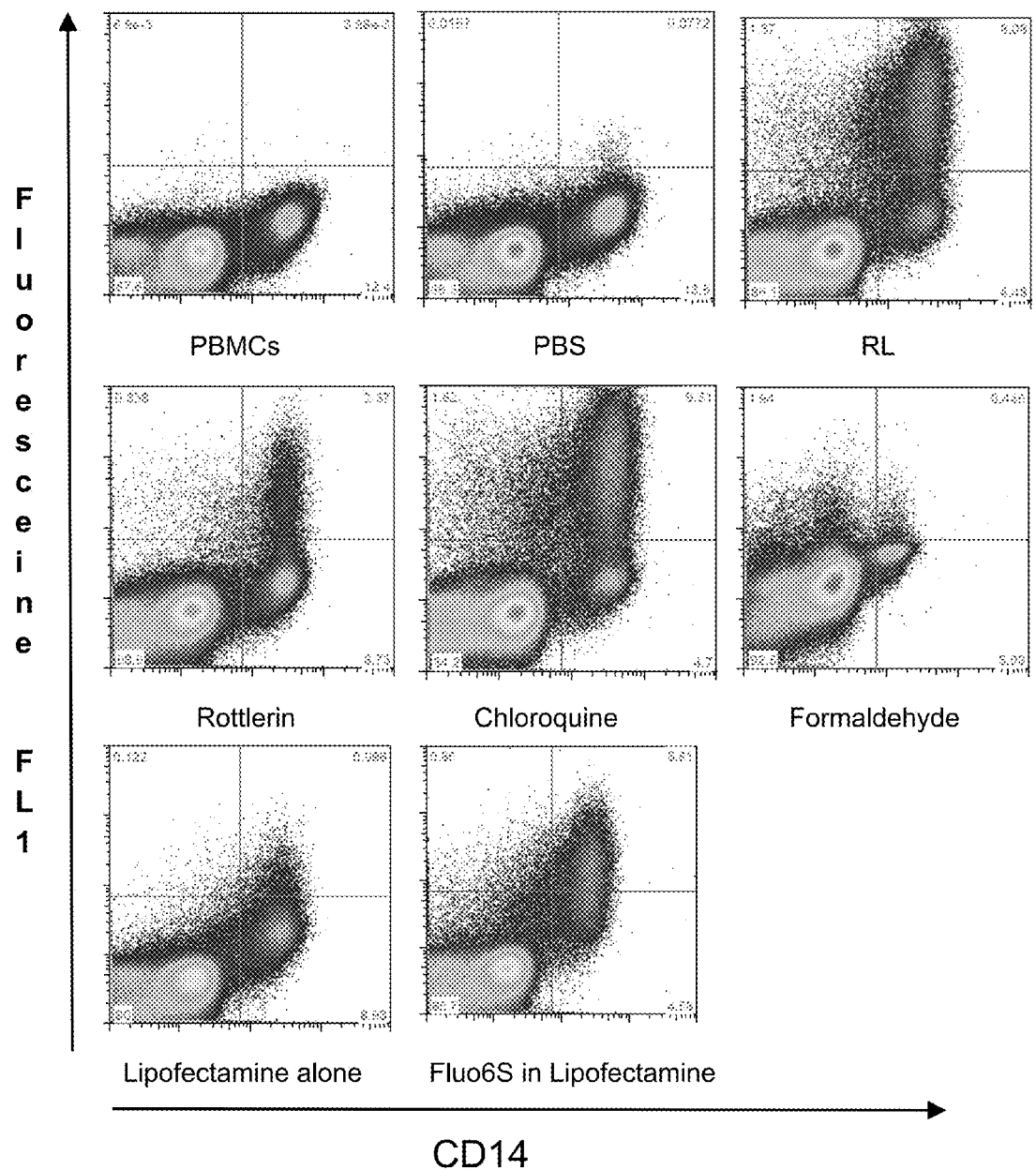

Formulated fluorescent RNA penetrates in tumor cells

PHARMACEUTICAL COMPOSITION CONSISTING OF RNA HAVING ALKALI METAL AS COUNTER ION AND FORMULATED WITH DICATIONS

FIELD OF THE INVENTION

The present invention relates to a biologically active RNA-alkali metal-dication formulation, a pharmaceutical composition containing said complexes and to a method of producing the same. The formulation of the present invention is particularly useful to introduce RNA and eventual attached cargo in cells allowing its biological intracellular activities: e.g. immunostimulation (immunomodulation), RNA interference or gene expression.

BACKGROUND OF THE INVENTION

Pharmaceutical Formulation of RNA

In addition to their central role as carriers of genetic information in the form of messenger RNA (mRNA), Ribonucleic Acid molecules (RNA) have recently been recognized to be pathogen-associated molecular patterns (PAMP) inducing immunostimulation (isRNA) and to be regulators of gene expression (antisense, small interfering RNA, siRNA and micro RNA, miRNA). All those natural activities of different types of naturally occurring RNA molecules can be reproduced using RNA produced in vitro (chemical or enzymatic synthesis) that are introduced in cells. Although exogenous naked nucleic acids (RNA or Deoxyribonucleic Acids, DNA) can be spontaneously taken up and biologically active in vivo [1], their activities are enhanced by methods (electroporation) or formulations (complexation by cationic polymers) aiming to favor their penetration in cells. Many reagents have been used to obtain such transfection of RNA molecules: cationic compounds like the peptide protamine [2] or polyethylenimine (PEI) [3, 4] or chitosan and/or lipophilic molecules such as cationic lipids that spontaneously form liposomes or micelles when mixed with nucleic acids in adequate conditions (recent review by Ozpolat et al. [5]). For clinical applications, those transfection reagents must be produced at pharmaceutical grade and mixed with RNA in a way that produces specified (size of particles, percentage of encapsulated RNA, etc.) formulations. The formulations may be more or less stable and toxic. Thus, alternatives which allow easy formulation of RNA for transfection of cells are needed. We here provide an invention and possible solution for this problem by demonstrating that RNA can penetrate cells, when it has an alkali metal (preferably sodium) as counter ion and when it is formulated in the presence of dication(s) (preferably calcium). Optimally, the RNA contains a poly-G (more than 2 consecutive G residues) or a poly-U (more than 4 consecutive U residues) or a GPurine$_{(n)}$G (where Purine is G or A residues and n from 1 to 4 or more) sequence. Those penetrating RNAs can bring an attached cargo (chemical or biological entity) inside cells.

Immunostimulating RNA (isRNA)

Immunostimulatory nucleic acid molecules include DNA comprising the unmethylated CpG motif (CpG oligodeoxynucleotide: CpG ODN), RNA in the form of double-stranded RNA (dsRNA), and stabilized, protected or otherwise chemically modified single-stranded RNA molecules (ssRNAs). The different families of nucleic acid PAMPs (i.e. CpG ODN, dsRNA, and ssRNA) are known to trigger different intracellular (located in endosomes) Toll-like receptors (TLRs) expressed by non-overlapping immune cell populations [6]. Those receptors give rise to different types of innate immune responses characterized by the secretion of a specific panel of cytokines including, but not limited to, for example, interleukine-6, Tumor Necrosis Factor (TNF)-alpha, or interferon-alpha. DNA triggers TLR-9, whereas dsRNA triggers TLR-3, and ssRNA triggers TLR-7 as well as TLR-8 (recently reviewed by Panter et al. [7]). For ssRNA, it was reported that RNA oligonucleotides stimulate preliminary through their U residues [3, 4]. Because exogenous stabilized ssRNA activates the innate immunity, it can be used as an adjuvant for vaccines as described by Scheel et al. for naked phosphorothioate RNA oligonucleotides [8] and Bourquin et al. [9] for liposome encapsulated RNA oligonucleotides.

Dielbold et al. [10] further showed that, when delivered to endosomes, viral and self RNA triggered equally efficiently TLR7 mediated innate immune response, further supporting the notion that discrimination between self and viral RNA ligands is based on endosomal accessibility rather than RNA sequence. Thus immunostimulation by exogenous RNA eventually linked to an antigen depends on the penetration of those molecules inside the cells. Thereby, isRNA must be formulated in transfection reagents. This step complicates the development of pharmaceutical isRNA and raises stability as well as toxicity issues.

The solution to the above technical problem is provided by the embodiments of the present invention as defined in the claims.

Protein Coding RNA (mRNA)

Long RNA molecules constitute the genome of some viruses (e.g. Influenza virus, HIV) and the intermediate genetic information between DNA and protein in all living cells. Such mRNA can be extracted from cells or produced in vitro by enzymatic transcription of linearized DNA plasmids, purified and used to transfect cells (reviewed by Pascolo [11]). In vitro transfection is routinely made thanks to electroporation or RNA-encapsulation. In the first case, mRNA is introduced in the cells by a short electric pulse. In the second case, lipids, most often cationic lipids or cationic peptides or cationic sugars are used to encapsulate mRNA, allowing its delivery in cells. Once in cells, mRNA is translated in proteins. In vivo, the direct skin injection of mRNA results in its spontaneous uptake by neighboring cells and expression [12]. However, for systemic expression after for example intra-peritoneal or intra-venous injections, encapsulation of the mRNA in delivery vehicles (cationic polymers and/or liposomes) is required. Systemic expression of the protein encoded by a therapeutic mRNA can be used with the goals of vaccination (triggering of a specific immune response against the encoded protein), immunomodulation (expression of an immunomodulating protein such as a cytokine) or gene therapy (expression of a protein such as insulin). Thus safe and robust methods to deliver mRNA are required. As mentioned above, formulations of RNA using cationic polymers or liposomes are associated to pharmaceutical and toxicity issues.

In view of these drawbacks, it would be highly desirable to have an mRNA composition that could result in systemic transfection of cells without the use of transfection polymers.

The solution to the above technical problem is provided by the embodiments of the present invention as defined in the claims.

Gene Interference RNA (Antisense RNA, siRNA or miRNA)

Single stranded antisense RNA, short interfering RNA (siRNA) in the form of a duplex of complementary synthetic oligonucleotides and micro RNA (miRNA) in the form of structured stem-loop RNA molecules, can target specifically (based on its sequence) a mRNA and block its translation and/or induce its cleavage that renders it dysfunctional. Antagomirs are oligonucleotides antisense to miRNA and can block miRNA's function. "Antisense" will thus stand here for anti-mRNA as well as anti-miRNA oligonucleotides. In particular, in vitro produced siRNAs are seen as very powerful tools for therapeutic intervention for achieving the specific degradation of "pathogenic mRNA", e.g. viral mRNA or oncogene mRNA. Since gene interference requires their intracellular localization, antisense and siRNA are formulated with polymers as above (PEI, cationic proteins, cationic sugars, liposomes, etc.) in order to be capable of efficiently penetrating cells after local (e.g. skin) or systemic (e.g. intravenous) injection. As mentioned above, formulations of RNA using cationic polymers or liposomes are associated with pharmaceutical and toxicity issues. In view of these drawbacks, it would be highly desirable to have antisense or siRNA formulations that could result in systemic transfection of cells without the use of transfection polymers.

The solution to the above technical problem is provided by the embodiments of the present invention as defined in the claims.

SUMMARY OF THE INVENTION

In particular, according to a first aspect, the present invention provides a cell penetrating RNA formulation. The formulation consists of an RNA molecule having an alkali metal (preferably Sodium) as counter ion and formulated in the presence of dication (preferably Calcium). At best, the RNA contains a poly-G (more than 2 consecutive G residues) or poly-U (more than 4 consecutive U residues) or GPurine$_{(n)}$G (where Purine is G or A residues and n from 1 to 4 or more) sequence. According to a second aspect, the present invention provides a pharmaceutical composition comprising the above formulated RNA for stimulation of Toll-Like Receptors (TLRs) and other intracellular sensors of immunity (e.g. Rig-1) resulting in triggering of immune modulation (stimulation or suppression of immune cells).

According to a third aspect, the present invention provides a pharmaceutical composition comprising the above formulated RNA in the form of mRNA for expression of proteins.

According to a fourth aspect, the present invention provides a pharmaceutical composition comprising the above formulated RNA in the form of single stranded antisense RNA (anti-mRNA or anti miRNA) or double stranded short RNA (siRNA) for specific modulation of gene expression.

According to a fifth aspect, the present invention provides a pharmaceutical composition comprising the above formulated RNA in the form of an hybrid molecule where the RNA sequence is linked to chemical or biological (e.g. DNA, Aptamer, lipid, sugar, peptide) moieties.

According to a sixth aspect, the present invention is directed to a method for the production of the pharmaceutical product as defined herein, which method comprises the steps of:

(a) Producing RNA in vitro using chemical or biological (enzymatic) synthesis (b) Setting alkali metal as counter ion of the RNA molecule (c) Adding Earth metal or other dications to the RNA preparation of above.

Preferably, the above step (a) is performed using chemical or biological synthesis followed by purification. Preferably, the RNA molecule has a poly-G (more than 2 consecutive G residues) or poly-U (more than 4 consecutive residues) or GPurine$_{(n)}$G (where Purine is G or A residues and n from 1 to 4 or more) sequence.

Preferably, the above step (b) is carried out by precipitating the RNA using sodium salts (sodium acetate for example) and alcohol (ethanol or isopropanol for example) or by performing a salt exchange chromatography. This step is followed by resuspending the RNA in aqueous solution and lyophilizing it by freeze drying.

Preferably, the above step (c) is made by adding a 1 to 20 mM $CaCl_2$ solution to a 1 to 10 mg/ml aqueous RNA solution (where the RNA has alkali metal as counter ion) resulting to a final concentration of Calcium of 0.2 to 20 mM.

Most preferred, the method according to the present invention comprises the following steps:

(a) Producing a RNA molecule that contains more than 2 consecutive G residues or more than 4 consecutive U residues or a GPurine$_{(n)}$G (where Purine is G or A residues and n from 1 to 4 or more)

(b) Precipitating this RNA using Sodium acetate and ethanol, resuspending the RNA in water and lyophilizing it by freeze-drying before resuspending it in water at 5 mg/ml (c) Adding Ringer lactate or comparable isotonic calcium-containing solution in order to bring the RNA to approximately 0.5 mg/ml final concentration.

In this context, it should be noted that, once the biologically active formulation is made, it can be further processed by for example dilution in relevant solutions before application to subjects (animal or human).

The present invention is based, at least in part, on the original discovery that RNA molecules can penetrate cells only when the RNA has an alkali metal as counter ion and when calcium (or possibly other dications) is then added to the RNA. At best, the RNA contains a poly-G (more than 2 consecutive G residues) or poly-U (more than 4 consecutive U residues) or GPurine$_{(n)}$G (where Purine is G or A residues and n from 1 to 4 or more) sequence. According to the current knowledge, it is assumed that the poly-G, poly U or GPurine$_{(n)}$G stretch allows the formation of tetrad (e.g. G-tetrads [13] or U-tetrads [14]) whereby four such sequences (eventually from four different RNA molecules) will associate thanks to "Hoogsteen" base pairing. Salts are known to affect the conformation of nucleic acid tetrads [15]. However, the impact of salts on the biological activity of ribonucleic acids produced in vitro and eventually containing tetrad-forming sequence was not so far studied. Our original results indicate that when the counter ion of RNA is sodium, but not when it is Triethylamine (TEA) (FIG. 1), and in the presence of Calcium (FIG. 2), RNA can penetrate or can be taken up by cells. The formation of defined complexes, presumably tetrads of RNA, is probably an event that is associated to the biological activity of our present new formulation. Since HPLC-purified RNA is used in research and development of nucleic acid-based drugs, the activity (efficient penetration in cells) that we describe here could not have been found earlier. Indeed, HPLC-purified RNA usually has TEA as counter ion. Such RNA, even when it contains favorable sequences (poly-G, poly U or GPurine$_{(n)}$G stretch) is not turned into biologically active RNA (cell penetrating RNA) by addition of calcium containing solution. The replacement of TEA by an alkali metal, in particular sodium, is a prerequisite to the capacity of the RNA to penetrate efficiently cells when formulated with calcium.

Another reason for the novelty of our invention is that calcium is needed in the formulation. Calcium-containing buffers are rarely used in research laboratories. Research reagents are dissolved in water or, when isotonic, cell-compatible solution is needed, in Phosphate Buffer Saline (PBS).

PBS does not contain dications. Thus, in standard laboratory, the activity of RNA molecules as described here even if the counter ion would has been sodium, would not have been discovered.

According to the present invention, the letter "G" means guanosine (guanine associated to a ribose)

According to the present invention, the letter "U" means uridine (uracil associated to a ribose)

According to the present invention, the letter "A" means adenosine (adenine associated to a ribose)

According to the present invention, the letter "C" means cytidine (cytosine associated to a ribose)

In the context of the present invention the term "Alkali metal" designates elements from the first column of the atom periodic classification; it includes Lithium (Li), Sodium (Na), Potassium (K), Rubidium (Rb), Caesium (Cs), Francium (Fr)

In the context of the present invention the term "Earth Metal" designates elements from the second column of the atom periodic classification; it includes Beryllium (Be), Magnesium (Mg), Calcium (Ca), Strontium (Sr), Barium (Ba), Radium (Ra)

In the context of the present invention the term "dication" designates earth metals (stable dications) as well as other metals that can acquire a double positive charge such as Chromium (Cr), Iron (Fe), Zinc (Zn), Silver (Ag), Scandium (Sc), Cobalt (Co), Copper (Cu), Lead (Pb), Mercury (Hg), Nickel (Ni), Tin (Sn), etc. Other complex dications consisting of several atoms are also included in the invention.

According to a preferred embodiment of the present invention, complexes of salts and RNA can be prepared by diluting an RNA having sodium as counter ion to less than 3 mg/ml but more than 0.1 mg/ml, preferably 0.5 mg/ml in Ringer lactate or other Calcium containing solution. Such complexes being undetectable by dynamic light scattering methods (not shown), they are smaller as 100 nm, thus remain polydispersed in solution and unlikely to physically disturb physiological processes such as blood circulation in capillary. Thus, the complexes have the additional benefit to be injectible, e.g. by intra venous injection.

According to a further preferred embodiment of the invention a Calcium concentration of 0.2 mM to 20 mM is used.

According to the present invention the presence of a poly-G (more than 2 consecutive G residues) or a poly-U (more than 4 consecutive U residues) or a GPurine$_{(n)}$G (where Purine is G or A residues and n from 1 to 4 or more) sequence in the RNA is helpful in order to get biologically active complexes (FIG. 3). A stretch of 6 consecutive G giving the maximal activity, it is the preferred sequence to be present in the RNA. Preferably, these sequences are at the extremity of the RNA molecule (5' or 3') (FIG. 4). Preferred RNA molecules of the present invention contain 6 to 10000 nucleotides. When isRNA or antisense RNA are to be formulated, the poly-G (more than 2 consecutive G residues) or poly-U (more than 4 consecutive U residues) or GPurine$_{(n)}$G (where Purine is G or A residues and n from 1 to 4 or more) sequence could be at the end of the molecule, for example the 3' end (FIG. 4A). When double stranded RNA such as siRNA are to be formulated, one strand of the RNA could carry a poly-G (more than 2 consecutive G residues) or a poly-U (more than 4 consecutive U residues) or a GPurine$_{(n)}$G (where Purine is G or A residues and n from 1 to 4 or more) sequence. It is preferentially the "sense" strand that would have it at its overhanging 3' end (FIG. 4B). When mRNA must be formulated, the poly-G (more than 2 consecutive G residues) or a poly-U (more than 4 consecutive U residues) or a GPurine$_{(n)}$G (where Purine is G or A residues and n from 1 to 4 or more) sequence could for example follow the poly-A tail at the 3' end of the mRNA (FIG. 4C)

The benefits of the present invention are independent of the RNA production method: chemical synthesis or biological synthesis using for example a RNA polymerase. The RNA can be linked to a cargo (a chemical or biological entity). As shown in FIG. 6 for fluorescein, the moiety attached to the adequately formulated RNA penetrates cells.

Poly-G containing CpG oligodeoxynucleotides (ODN) which are DNA molecules are known to spontaneously form tetrads that allows their biological activity of immunostimulation [16]. Thus, DNA oligonucleotides structured in G-tetrads can penetrate in cells. On the contrary, we surprisingly found that standard HPLC purified RNA oligonucleotides containing a poly-G sequence of 6 consecutive G residues does not show biological activity even when formulated with Calcium-containing buffer (FIG. 1). Standard HPLC-purification methods for RNA molecules use Reverse Phase technology. Thereby, TEA is the counter ion of the final RNA product. In those conditions, the addition of a calcium containing solution does not result in the generation of the biologically active (cell-penetrating) complexes (FIG. 1). Only when TEA is replaced by Sodium can the RNA form active complexes after addition of calcium-containing solution (FIG. 1).

Because the raw synthesis product of chemically synthesized RNA molecules can contain several contaminants including partially deprotected RNA and abortive sequences (shorter than the expected oligoribonucleotide) as well as aberrant sequences (longer or shorter than the expected oligoribonucleotide), researchers routinely purchase HPLC purified oligonucleotides. Indeed, contaminants may have biological activities independent of the activity of the expected sequence. Thereby they could hide or increase or induce biological activities and generate misleading results. Accordingly, companies producing oligonucleotides often offer only HPLC purified product, guarantying highest quality for accurate biological testing. Only few companies, including Thermo (Ulm, Germany) offer unpurified RNA oligonucleotides, termed "desalted". In that case, after their synthesis, the oligonucleotides are deprotected and then recovered by precipitation using sodium acetate and ethanol. Thereafter, they are resuspended in water, quantified by optical Density and lyophilized by freeze drying. As a result of this treatment, they have sodium as counter ion. On the contrary, because HPLC purification use TEA-buffers, purified RNA oligonucleotides have TEA as counter ion.

Biological activities found to be triggered by unpurified (i.e. "desalted") RNA oligonucleotides and not by HPLC purified RNA oligonucleotides would be intuitively classified as artefactual, due to contaminants, and disregarded. However, we discovered here that this situation, as well as the reverse situation (biological activity triggered or enhanced by purified RNA oligonucleotide but not by the unpurified version) could not only be due to the presence of contaminants in one (unpurified) and not in the other (purified) RNA product but to the counter ion associated to the RNA. The functional discrepancy between unpurified and purified RNA oligonucleotides (identical sequence) in term of biological activity (for example production of cytokine such as interferon-alpha by penetration in immune cells and triggering of intracellular Toll Like Receptors) as seen in FIG. 1 could have been explained by the fact that contaminants, for example partially deprotected RNA oligonucleotides that still contain chemical moieties blocking reactive groups of the RNA during its synthesis, had the biological activity but not the expected pure RNA sequence. However, as we show in FIG. 1, the biological activity of the HPLC purified RNA oligonucleotide is recovered after it has been precipitated by sodium acetate/ethanol, thus having sodium as counter ion. Thanks to this series of experiment, we could discover and document that for penetration of RNA after formulation in dication-containing solution, it is important that the purified RNA is processed in order to have an alkali metal, in particular sodium, as counter ion.

Besides specificity of the counter ion, our discovery (penetrating RNA) requires another element: the presence of dication, in particular calcium. Thus, calcium is the preferred dication to be used to formulate RNA into a biologically active formulation. In addition, at best the RNA sequence would contain a poly-G (more than 2 consecutive G residues) or a poly-U (more than 4 consecutive U residues) or a Gpurine$_{(n)}$G (where Purine is G or A residues and n from 1 to 4 or more).

Modifications on the RNA residues may be used to enhance or reduce the triggering of certain biological reactions. For example, phosphorothioate backbone (replacement of one oxygen atom on the phosphate link between nucleotides by a sulfur atom), Locked Nucleic Acids (LNA) or Peptide Nucleic Acids (PNA) may be use to render the RNA more stable and more resistant toward RNases. Another example is the modification of certain residues such as primarily U or G residues in order to avoid recognition by Toll Like Receptors and other immunomodulating receptors. This allows formulated antisense RNA, siRNA or mRNA to produce their biological activity (regulation of gene expression or expression of a protein, respectively) without triggering immune stimulation.

Other objects, advantages and novel features of the present invention will become apparent from the following detailed description when considered in conjunction with the accompanying drawings.

BRIEF DESCRIPTION OF THE DRAWINGS

FIG. 4 depicts the possible sequence or structure of (A) isRNA or antisense RNA, (B) siRNA (N stands for ribonucleotide or modified ribonucleotide or deoxyribonucleotide) and (C) mRNA ("(A)" means more than 10 A residues) according to the invention.

FIGS. 6A and 6B show that cells take up fluorescent RNA.

DETAILED DESCRIPTION OF THE INVENTION

Figure 1A:
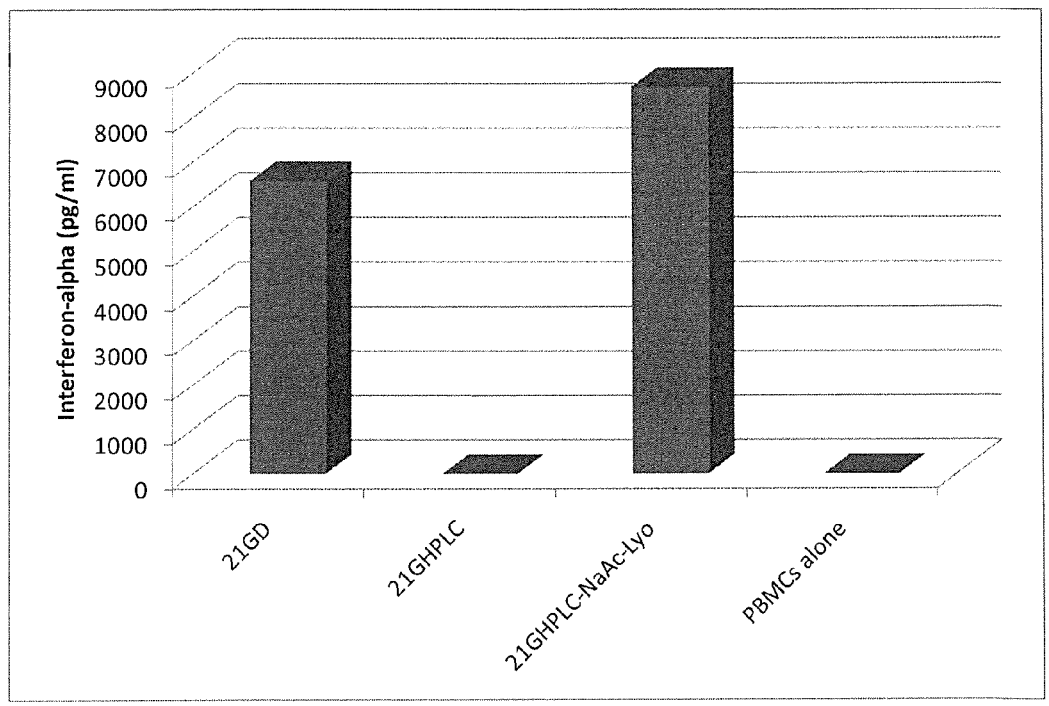
FIGS. 1A and 1B show that RNA formulated in Ringer Lactate is biologically active when sodium is the counter ion of the RNA.

As opposed to what is described in the prior art, the present inventor surprisingly discovered that RNA can efficiently penetrate cells in the absence of polymeric transfection reagents or electric pulse. For this, the RNA must:
  (i) have as counter ion an alkali metal (Lithium (Li), Sodium (Na), potassium (K), Rubidium (Rb), Caesium (Cs), Francium (Fr)), preferentially Sodium
  (ii) be formulated in the presence of a earth metal (Beryllium (Be), Magnesium (Mg), Calcium (Ca), Strontium (Sr), Barium (Ba), Radium (Ra)), preferentially Calcium or other dications.

In addition, at best the RNA should contain a specific sequence such as poly-G (more than 2 consecutive G residues) or a poly-U (more than 4 consecutive U residues) or a GPurine$_{(n)}$G (where Purine is G or A residues and n from 1 to 4 or more) sequence.

A preferred procedure for the preparation of such transfectable RNA is to set sodium as the counter ion of the RNA by precipitating HPLC-purified molecules by sodium acetate/ethanol, resuspend at 5 mg/ml in water and then formulate the RNA to 0.5 mg/ml using Calcium containing solutions such as Ringer Lactate.

It was also found that no detectable particles or aggregates are formed in the present formulations. Thus, making it injectable even intra-venous.

RNA molecules used in research are usually HPLC purified. Thereby, contaminants such as abortive sequences (shorter than the required sequence) or aberrant sequences (longer than the required sequence) as well as, for chemical synthesis, not fully deprotected sequences, are eliminated. This is important as such contaminants may bring biological activities in the experiments that are not specific to the desired RNA. HPLC purification of RNA requires several buffers usually containing triethylamine (TEA). This cation associates to RNA and remains its counter ion in the final purified RNA product. Applications of the invention:

isRNA (Immunostimulating Single Stranded RNA of More than 6 Residues)

A benefit of the present invention is that when formulating an unmodified U and/or G-containing RNA, a strong production of interferon-alpha is induced. Interferon-alphas represent the cytokines exhibiting the longest record of use in clinical oncology for the treatment of over a dozen of cancer types, including some hematological malignancies and solid tumors (e.g. renal cell carcinoma or cutaneous melanoma) [17]. Interferon-alpha is also used against Hepatitis C virus. Based on the non-specific immunostimulation characteristic of the present invention, it can be used to activate or strengthen the immunity against chronic diseases such as cancer or persistent virus infections. It can also be used to modulate autoimmunity.

Examples of cancers treatable with the immunostimulating composition, according to the invention include malignant melanoma, all types of carcinoma (colon, renal cell, bladder, prostate, non-small cell and small cell lung carcinoma, etc.), lymphomas, sarcomas, blastomas, gliomas, etc.

Examples of infectious diseases treatable with the immunostimulating composition, according to the invention include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), bacterial infectious diseases, such as Legionnaire's disease (*Legionella*), gastric ulcer (*Helicobacter*), cholera (*Vibrio*), infections by *E. coli*, Staphylococci, *Salmonella* or Streptococci (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans*, *Histoplasma capsulatum*, *Coccidioides immitis*, *Blastomyces dermatitidis* or *Candida albicans*).

By switching immunity, the immunostimulating pharmaceutical composition of the present invention may prove to be useful to treat allergies as well.

The RNA used to prepare the isRNA formulation could be an oligonucleotide that has the following sequences (written 5' to 3'): AGUGUUAUCUUGUAUGGGGGG (SEQ ID NO: 1). The RNA could be physically linked to a moiety of interest such as a peptide.

Because manufacturing of oligonucleotides by chemical synthesis is easier in very large scales (kilograms) than the enzymatic synthesis of RNA, oligoribonucleotides to use for formulating isRNA are preferably produced by chemical synthesis.

As used herein, the term "oligoribonucleotide" shall mean multiple ribonucleotides (i.e. a molecule comprising a ribose) linked to a phosphate group and to an organic base selected from the group consisting of cytosine (C), uracil (U) adenine (A) and guanine (G). An oligomer generally is defined to consist of a finite number of monomer units, which number ranges from a few to more than a hundred. In the context of the present invention, an oligoribonucleotide consists of about 6 to 100 ribonucleotides. Preferably, 12 to 40 and even more preferably 16 to 24.

The RNA contained in the present isRNA invention is preferably single-stranded and usually does not contain chemical modifications to its subunits (e.g. on the base, or on the phosphate, or on the ribose residue). However, modifications (e.g. phosphorothioate backbone, peptide nucleic acid: PNA, backbone, 2' Fluoro) that could help manufacturing or formulation or biological activities or linkage to a cargo of the isRNA described herein are also subject of the present invention. The 5' end of the RNA can be OH, monophosphate or triphosphate, the later allowing stimulation of the cytosolic RIG-1 and enhancing immunostimulation.

Apart from the preferred poly-G (more than 2 consecutive G residues) or poly-U (more than 4 consecutive U residues) or GPurine(n)G (where Purine is G or A residues and n from 1 to 4) sequence, there is no specific sequence requirement for an oligoribonucleotide molecule to be suitable for preparing the isRNA composition according to the present invention. Preferably, however, the RNA contains at least 25% uridine residues. One or several oligonucleotide sequences can be combined to generate the isRNA formulation according to the present invention. Attachment to a cargo (e.g. peptide) can be used so that the formulated RNA brings relevant moieties in cells.

To further increase effectiveness, the immunostimulating compositions according to the invention can comprise one or more adjuvants, preferably to achieve a synergistic effect of immunostimulation. "Adjuvant" in this context encompasses any compound which promotes an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, gp96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances are to be considered. Because of the presence of the immunostimulating agent according to the invention comprising RNA as the primary immunostimulant, however, only a relatively small amount of CpG DNA is necessary (compared with immunostimulation with only CpG DNA). Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CFS, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also particularly suitable for use as further adjuvants in the immunostimulating composition of the present invention.

In a preferred embodiment, the immunostimulating composition according to the invention can also be used in conjunction with another therapeutic reagent. The immunostimulatory RNA composition of the present invention may on its own synergize with other treatments such as chemotherapeutic drugs for cancer patients or highly active anti retrovirus therapy (e.g. tri-therapy) for HIV-infected patients or chloroquine, a drug used against malaria infection and known to improve cross priming. Indeed, the immunostimulating composition alone is able to induce a nonspecific general activation of the immune system, which in turn helps the control of pathogens.

Many chemotherapy regimens (gemcitabine, etopophos, cis-platin, carbo-platin, etc.) or radiotherapy protocols can be used at dosages that do not severely affect the immune system. Thus, during radio/chemotherapy in cancer patients, immunomodulation can be used whereby the death of tumor cells can be accompanied by the enhanced induction of an immune response using immunostimulating compositions according to the present invention. Systemic (intra-venous or sub-cutaneous for example) as well as local (intra-tumor or intradermal for example) injections of an isRNA composition according to the present invention in patients under radio/chemotherapy may help the immune system to increase a response against the tumor. This immune response could also control tumor growth. In a further embodiment, the pharmaceutical composition of the present invention takes the form of a vaccine preparation comprising the isRNA defined above and at least one antigen. Adaptive immune responses to specific antigens, i.e. immune responses primarily mediated by professional APCs, T-cells, and B-cells, can be augmented, if a stimulus through TLRs for example occurs simultaneously, shortly before (within hours up to 48 hours), or soon after administration of a vaccine (foreign or self antigens, wild type or mutated). An "antigen" is to be understood as meaning any structure which can cause the formation of antibodies and/or the activation of an adaptive cellular immune response. Examples of antigens are polypeptides, proteins, cells, cell extracts, carbohydrates/polysaccharides, polysaccharide conjugates, lipids, and glycolipids. These antigens may be tumor antigens or viral, bacterial, fungal and protozoological antigens or allergens. The antigen may be present in the vaccine according to the invention in the form of a hapten coupled to the RNA or a suitable carrier. Suitable carriers are known to those ordinarily skilled in the art and include e.g. human serum albumin (HSA), polyethylene glycols (PEG). The hapten may be coupled to the carrier by processes well-known in the prior art, e.g. in the case of a polypeptide carrier via an amide bond to a Lys residue. The formulation of antigen plus isRNA may be formulated as an emulsion using mixing with an oil such as Montanide®.

In an alternative embodiment, the immunostimulating composition of the present invention may be used in genetic vaccination, wherein an immune response is stimulated by introduction into the organism or into the cell (direct injection by needle-dependent or needle-less devices or in vitro electroporation followed by adoptive transfer of cells) of a suitable nucleic acid molecule which codes for this antigen.

This nucleic acid molecule may be a DNA or a mRNA. The isRNA formulated according to the present invention can be injected systematically (intra-venous or sub-cutaneous) as well as locally at the site of DNA or mRNA delivery (eventually co-delivered), thereby providing an immune environment (induction of cytokines and maturation of APCs) profitable to the induction of an immune response.

The vaccine strategies according to the invention are suitable for the treatment of cancers. A tumor-specific antigen (TSA) or a nucleic acid which codes for such an antigen as well as part(s) of tumor antigens or nucleic acids which code for such part(s) may be used in this context. Specific examples of tumor antigens which can be used according to the invention include but is not limited to 707-AP, AFP, ART-4, BAGE, .beta.-catenin/m, Bcr-abl, CAMEL, CAP-1, CASP-8, CDC27/m, CDK4/m, CEA, CT, Cyp-B, DAM, ELF2M, ETV6-AML1, G250, GAGE, GnT-V, Gp100, HAGE, HER-2/neu, HLA-A*0201-R1701, HPV-E7, HSP70-2M, HAST-2, hTERT (or hTRT), iCE, KIAA0205, LAGE, LDLR/FUT, MAGE, MART-1/Melan-A, MC1R, myosin/m, MUC1, MUM-1, -2, -3, NA88-A, NY-ESO-1, p190 minor bcr-abl, Pml/RAR.alpha., PRAME, PSA, PSM, RAGE, RU1 or RU2, SAGE, SART-1 or SART-3, TEL/AML1, TPI/m, TRP-1, TRP-2, TRP-2/INT2 and WT1.

The vaccine according to the invention may be furthermore employed against infectious diseases.

The immunomodulating drug according to the invention may be used in combination with chloroquine, a pharmaceutical compound that impacts intracellular distribution (leakage from endosomes) and that also increases cross presentation and thus the induction of antigen-specific effector T-cells.

The present isRNA invention is particularly suitable for use in inducing production, or increasing the level of, IFN-alpha. When added to human PBMC cells in vitro, the immunostimulating composition is capable of inducing production of at least 500 pg/ml interferon IFN-alpha by 1 million human PBMCs cultivated 24 hours in 200 μl culture medium (RPMI plus 10% fetal calf serum).

A further embodiment is an injectible formulation comprising the isRNA of the invention in combination with a pharmaceutically acceptable excipient such as Ringer Lactate.

The present invention further provides a method of immunostimulation, in particular for stimulating a host immune response in a subject, preferably a mammal, especially a human. An effective amount of a pharmaceutical composition according to the invention is administered, optionally in combination with another therapeutic treatment (for example, radiotherapy) or agent, such as a protein vaccine, a cancer chemotherapy agent, an additional immunomodulating agent, a pharmaceutical drug modifying intracellular distribution and/or enhancing cross-priming such as chloroquine, an antiviral agent, anti-parasite agent or an antibacterial agent. Thus, the present invention also comprises the use of penetrating RNA formulation as defined herein for the preparation of a pharmaceutical composition or medicament for immunomodulation, in particular for stimulating the host immune response in a subject, preferably a mammal, especially a human.

Preferably, the additional immunomodulating agent is an anti-CTLA-4 or anti-regulatory T-cell reagent such as an anti-CD25 antibody or cyclophosphamide.

The at least one additional therapeutic agent may be administered simultaneously with the pharmaceutical composition, or the at least one additional therapeutic agent is administered sequentially with the pharmaceutical composition.

According to the method of the present invention, IFN-alpha level is increased by the administration of the immunostimulating composition of the invention.

In a further embodiment, the present invention provides an ex vivo method for stimulating and transfecting (cargo attached to the RNA) host immune response in a mammal. In one embodiment, suitable immune cells are isolated from the mammal and are treated in vitro via administering to the isolated immune cells an effective amount of a pharmaceutical composition of the present invention, and the stimulated immune cells are re-introduced into the organism. Suitable immune cells for such ex vivo treatment include but are not limited to dendritic cells.

The method and composition of the present invention may be used to supplement interferon-α treatment, or to increase interferon-α in a subject. The method and composition of the present invention may be used to supplement interferon treatments, or to increase interferons (e.g. alpha, beta or lambda) in a subject.

The immunostimulating composition of the invention comprises, in addition to RNA and salts, and other therapeutic or immunogenic agents, a pharmaceutically acceptable carrier and/or a pharmaceutically acceptable vehicle and/or pharmaceutically acceptable diluent. Appropriate routes for suitable formulation and preparation of the immunostimulating agent according to the invention and the vaccine are disclosed in Remington: "The Science and Practice of Pharmacy," 20th Edn., A. R. Gennaro, Editor, Mack Publishing Co., Easton, Pa. (2003). Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxy-propylene copolymers. Immunostimulating agents and vaccines according to the invention can comprise filler substances or substances such as lactose, mannitol, substances for covalent linking of polymers, or inclusion of materials in or on particular preparations of polymer compounds, such as e.g. polylactate, polyglycolic acid, hydrogel or to liposomes, microemulsions, micelles, unilamellar or multilamellar vesicles, erythrocyte fragments or spheroblasts. The particular embodiments of the immunostimulating agent and the vaccine are chosen according to the physical properties, for example in respect of solubility, stability, bioavailability or degradability. Controlled or constant release of the active drug (-like) components according to the invention includes formulations based on lipophilic depots (e.g. fatty acids, waxes or oils). Immunostimulating substances or compositions according to the invention can furthermore have protective coatings, e.g. protease inhibitors or permeability intensifiers. Preferred carriers are typically aqueous carrier materials, water for injection (WFI) or water buffered with phosphate, citrate, HEPES or acetate, or Ringer or Ringer Lactate etc. being used, and the pH is typically adjusted to 5.0 to 8.0, preferably 6.5 to 7.5. The carrier or the vehicle will additionally preferably comprise salt constituents, e.g. sodium chloride, potassium chloride or other components which render the solution e.g. isotonic. Furthermore, the carrier or the vehicle can contain, in addition to the above-mentioned constituents, additional components, such as human serum albumin (HSA), polysorbate 80, sugars or amino acids.

The mode and method of administration and the dosage of the immunostimulating agent according to the invention depend on the nature of the disease to be treated, where appropriate the stage thereof, the antigen (in the case of the vaccine) and also the body weight, the age and the sex of the patient.

The immunostimulating composition of the present invention may preferably be administered to the patient parenterally, e.g. intravenously, intraarterially, subcutaneously, intradermally, intra-lymph node or intramuscularly. It is also possible to administer the immunostimulating agent or the vaccine topically or orally. A further injection possibility is into a tumor tissue or tumor cavity (after the tumor is removed by surgery, e.g. in the case of brain tumors).

mRNA (Single Stranded RNA of More than 100 Residues)

A benefit of the present invention is that when formulating a coding RNA (mRNA in general with the following structure: 5' cap, coding sequence starting with a start codon and ending with a stop codon, untranslated 3' end followed by a poly-A tail) that at best contains a poly-G (more than 2 consecutive G residues) or a poly-U (more than 4 consecutive U residues) or a GPurine(n)G (where Purine is G or A residues and n from 1 to 4 or more) sequence(s), it can penetrate cells thereby allowing transient transgenic protein expression. Messenger RNA coding for a protein of interest can be produced in vitro by transcription using for example a plasmid DNA matrix. If needed, a poly-G (more than 2 consecutive G residues) or a poly-U (more than 4 consecutive U residues) or a GPurine(n)G (where Purine is G or A residues and n from 1 to 4 or more) sequence can for example be added after the poly-A tail by adding in the DNA matrix a poly-dG (more than 2 consecutive dG residues) or a poly-dT (more than 4 consecutive dT residues) or a dGdPurine(n)dG (where dPurine is dG or dA residues and n from 1 to 4 or more) sequence (d stands for deoxy). Alternatively, poly-G or poly-U sequences can be added to the mRNA using terminal transferase.

There are two main utilizations of mRNA in therapeutical settings: vaccination and gene therapy.

i—Vaccination

A preferred mRNA vaccine according to the invention (alkali metal as counter ion and dication in formulation) will code for one or several antigen(s).

Such a vaccine could be used to stimulate specifically anti cancer immunity. Specific examples of tumor antigens which can be used according to the invention include but is not limited to 707-AP, AFP, ART-4, BAGE, .beta.-catenin/m, Bcr-abl, CAMEL, CAP-1, CASP-8, CDC27/m, CDK4/m, CEA, CT, Cyp-B, DAM, ELF2M, ETV6-AML1, G250, GAGE, GnT-V, Gp100, HAGE, HER-2/neu, HLA-A*0201-R1701, HPV-E7, HSP70-2M, HAST-2, hTERT (or hTRT), iCE, KIAA0205, LAGE, LDLR/FUT, MAGE, MART-1/Melan-A, MC1R, myosin/m, MUC1, MUM-1, -2, -3, NA88-A, NY-ESO-1, p190 minor bcr-abl, Pml/RAR.alpha., PRAME, PSA, PSM, RAGE, RU1 or RU2, SAGE, SART-1 or SART-3, TEL/AML1, TPI/m, TRP-1, TRP-2, TRP-2/INT2 and WT1.

The vaccine according to the invention may be furthermore employed against infectious diseases. Thereby the mRNA will code for one or several pathogen-derived proteins. The pathogen could be for example Human Immunodeficiency Virus (HIV), Hepatitis B virus (HBV), Hepatitis C virus (HCV), *Chlamydophila* pneumonia, etc.

Examples of cancers treatable or preventable by the mRNA composition, according to the invention include malignant melanoma, all types of carcinoma (colon, renal cell, bladder, prostate, non-small cell and small cell lung carcinoma, etc.), lymphomas, sarcomas, blastomas, gliomas, etc.

Examples of infectious diseases treatable or preventable by the mRNA composition, according to the invention include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), bacterial infectious diseases, such as Legionnaire's disease (*Legionella*), gastric ulcer (*Helicobacter*), cholera (*Vibrio*), infections by *E. coli*, Staphylococci, *Salmonella* or Streptococci (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans, Histoplasma capsulatum, Coccidioides immitis, Blastomyces dermatitidis* or *Candida albicans.*

By triggering and re-directing specific immunity, the mRNA vaccine composition of the present invention may prove to be useful to treat allergies as well. In this context the mRNA will encode relevant allergen proteins such as bee-venom.

Apart from the preferred poly-G (more than 2 consecutive G residues) or poly-U (more than 4 consecutive U residues) or GPurine(n)G (where Purine is G or A residues and n from 1 to 4 or more) sequence(s), there is no specific ribonucleotide sequence requirement for a mRNA molecule to be suitable for preparing the mRNA vaccine composition according to the present invention. Preferably, however, the mRNA contains unmodified uridine residues. Thereby, the mRNA vaccine will trigger non specific immunomodulation through Toll Like Receptors that will provide adequate help for the triggering of protein (encoded by the mRNA)-specific immunity. One or several mRNA sequences can be combined to generate the mRNA formulation according to the present invention.

To further increase effectiveness, the mRNA vaccine according to the invention can comprise one or more adjuvants, preferably to achieve a synergistic effect of immunostimulation. "Adjuvant" in this context encompasses any compound which promotes an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances are to be considered. Because of the presence of the immunostimulating agent according to the invention comprising RNA as the primary immunostimulant, however, only a relatively small amount of CpG DNA is necessary (compared with immunostimulation with only CpG DNA). Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CFS, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also particularly suitable for use as adjuvants in the mRNA vaccine composition of the present invention.

In a preferred embodiment, the mRNA vaccine according to the invention can also be used in conjunction with another therapeutic reagent. The mRNA vaccine composition of the present invention may on its own synergize with other treatments such as chemotherapeutic drugs for cancer patients or highly active anti retrovirus therapy (e.g. tritherapy) for HIV patients or chloroquine, a drug used against malaria infection and known to modify intracellular distributions (leakage from endosomes) and improve cross priming. Many chemotherapy regimens (gemcitabine, etopophos, cis-platin, carbo-platin, etc.) or radiotherapy protocols can be used at dosages that do not severely affect the immune system. Thus, during radio/chemotherapy in cancer patients, vaccination can be used whereby the death of tumor cells induced by chemo-, radio-therapy can be enhanced by the presence of a specific immune response induced by the mRNA-vaccine compositions according to the present invention. Vaccinating patients under radio/chemotherapy before or after their treatment may help the therapeutic response of the tumor.

The present invention further provides a method of vaccination, in particular for stimulating a host immune response in a subject, preferably a mammal, especially a human. An effective amount of a mRNA vaccine pharmaceutical composition according to the invention is administered, optionally in combination with another therapeutic treatment (for example, radiotherapy) or agent, such as a cancer chemotherapy agent, an additional vaccine, an additional immunomodulating agent, a pharmaceutical drug enhancing cross-priming such as chloroquine, an antiviral agent, anti-parasite agent or an anti-bacterial agent. Thus, the present invention also comprises the use of penetrating messenger RNA formulation as defined herein for the preparation of a pharmaceutical composition or medicament for vaccination, in particular for specifically stimulating the host adaptive immune response in a subject, preferably a mammal, especially a human.

Preferably, the additional immunomodulating agent is an anti-CTL-A-4 or anti-regulatory T-cell reagents such as an anti-CD25 antibody or cyclophosphamide.

The at least one additional therapeutic agent may be administered simultaneously with the pharmaceutical mRNA composition, or the at least one additional therapeutic agent is administered sequentially with the mRNA pharmaceutical composition.

In a further embodiment, the present invention provides an ex vivo method for transfecting mRNA in host immune cells. In one embodiment, suitable immune cells are isolated from the mammal and are treated in vitro via administering to the isolated immune cells an effective amount of a pharmaceutical mRNA composition of the present invention, and the treated (transfected) immune cells are re-introduced into the organism. Suitable immune cells for such ex vivo treatment include but are not limited to dendritic cells.

The mRNA vaccine composition of the invention comprises, in addition to mRNA having adequate salts (alkali metal as counter ion and dications in formulation) and other therapeutic or immunogenic agents, a pharmaceutically acceptable carrier and/or a pharmaceutically acceptable vehicle and/or pharmaceutically acceptable diluent. Appropriate routes for suitable formulation and preparation of the mRNA vaccine according to the invention are disclosed in Remington: "The Science and Practice of Pharmacy," 20th Edn., A. R. Gennaro, Editor, Mack Publishing Co., Easton, Pa. (2003). Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxy-propylene copolymers. Messenger mRNA vaccines according to the invention can comprise filler substances or substances such as lactose, mannitol, substances for covalent linking of polymers, or inclusion of materials in or on particular preparations of polymer compounds, such as e.g. polylactate, polyglycolic acid, hydrogel or to liposomes, microemulsions, micelles, unilamellar or multilamellar vesicles, erythrocyte fragments or spheroblasts. The particular embodiments of the mRNA vaccine are chosen according to the physical properties, for example in respect of solubility, stability, bioavailability or degradability. Controlled or constant release of the active drug (-like) components according to the invention in the vaccine includes formulations based on lipophilic depots (e.g. fatty acids, waxes or oils). In the context of the present invention, coatings of vaccine substances according to the invention, namely coatings with polymers, are also disclosed (e.g. polyoxamers or polyoxamines). Vaccine substances or compositions according to the invention can furthermore have protective coatings, e.g. protease inhibitors or permeability intensifiers. Preferred carriers are typically aqueous carrier materials, water for injection (WFI) or water buffered with phosphate, citrate, HEPES or acetate, or Ringer or Ringer Lactate etc. being used, and the pH is typically adjusted to 5.0 to 8.0, preferably 6.5 to 7.5. The carrier or the vehicle will additionally preferably comprise salt constituents, e.g. sodium chloride, potassium chloride or other components which render the solution e.g. isotonic. Furthermore, the carrier or the vehicle can contain, in addition to the abovementioned constituents, additional components, such as human serum albumin (HSA), polysorbate 80, sugars or amino acids.

The mode and method of administration and the dosage of the mRNA vaccine according to the invention depend on the nature of the disease to be treated, where appropriate the stage thereof, and also the body weight, the age and the sex of the patient.

The mRNA vaccine of the present invention may preferably be administered to the patient parenterally, e.g. intravenously, intraarterially, subcutaneously, intradermally, intra-lymph node or intramuscularly. It is also possible to administer the vaccine topically or orally. A further injection possibility is into a tumor tissue or tumor cavity (after the tumor is removed by surgery, e.g. in the case of brain tumors).

ii—Gene Therapy

A preferred mRNA gene therapy drug according to the invention alkali metal as counter ion, dication in formulation and eventually poly-G (more than 2 consecutive G residues) or poly-U (more than 4 consecutive U residues) or GPurine (n)G (where Purine is G or A residues and n from 1 to 4 or more) sequence(s) will code for one or several therapeutically relevant protein.

Such a mRNA could preferably be used to express a protein for which the two copies of a gene are missing or mutated in the patient, causing a disease (autosomal recessive or X-linked genetic disorder). Specific examples of mutated protein associated to a disease and which could be treated according to the invention include hemoglobin (Sickle Cell Anemia), HFE (hemochromatosis), cystic fibrosis transmembrane conductance regulator (cystic fibrosis), Interleukine 2 receptor gamma chain (Severe combined immunodeficiency disease).

Apart from the preferred poly-G (more than 2 consecutive G residues) or poly-U (more than 4 consecutive U residues) or GPurine(n)G (where Purine is G or A residues and n from 1 to 4 or more) sequence(s), there is no further specific ribonucleotide sequence requirement for a mRNA molecule to be suitable for preparing the mRNA gene therapy composition according to the present invention. Preferably, however, the mRNA contains modified residues, in particular modified U (e.g. pseudouridine) and/or G residues. Thereby, the mRNA gene vehicle will not trigger non-specific immunomodulation through Toll Like Receptors. Hence, the therapeutic mRNA would not provide help for the triggering of protein (encoded by the mRNA)-specific immunity. As a result, there will be no specific immune response against the therapeutic mRNA-encoded protein. One or several mRNA sequences can be combined to generate the mRNA gene therapy formulation according to the present invention.

To further increase effectiveness, the mRNA gene therapy vehicle according to the invention can comprise one or more immunosuppressant agent. "Immunosuppressant agent" in this context encompasses any compound which suppresses an immune response. Particularly preferred immunosuppressing drugs are cyclosporine, cyclophosphamide, anti-lymphocyte antibodies (e.g. anti CD20) or anti-cytokine antibodies (e.g. anti-TNF-alpha).

In a preferred embodiment, the mRNA gene therapy vehicle according to the invention can also be used in conjunction with another therapeutic reagent. An effective amount of a pharmaceutical composition according to the invention is administered, optionally in combination with another therapeutic treatment or agent, such as an immuno-suppressing drug.

In a further embodiment, the present invention provides an ex vivo method for transfecting mRNA in relevant host cells (e.g. stem cells). In one embodiment, suitable cells are isolated from the mammal, eventually differentiated in vitro and incubated with an effective amount of a pharmaceutical mRNA composition of the present invention. Thereafter, the treated (transfected) cells are re-introduced into the organism.

The mRNA gene therapy composition of the invention comprises, in addition to adequate salts (alkali metal as counter ion and dications in formulation) and eventually other therapeutic or immunosuppressing agents, a pharmaceutically acceptable carrier and/or a pharmaceutically acceptable vehicle and/or pharmaceutically acceptable diluent. Appropriate routes for suitable formulation and preparation of the mRNA gene therapy vehicle according to the invention are disclosed in Remington: "The Science and Practice of Pharmacy," 20th Edn., A. R. Gennaro, Editor, Mack Publishing Co., Easton, Pa. (2003). Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxy-propylene copolymers. The particular embodiments of the gene therapy formulation are chosen according to the physical properties, for example in respect of solubility, stability, bioavailability or degradability.

Controlled or constant release of the active drug (-like) components according to the invention includes formulations based on lipophilic depots (e.g. fatty acids, waxes or oils). In the context of the present invention, coatings of vaccine substances according to the invention, namely coatings with polymers, are also disclosed (e.g. polyoxamers or polyoxamines). The gene therapy substances or compositions according to the invention can furthermore have protective coatings, e.g. protease inhibitors or permeability intensifiers. Preferred carriers are typically aqueous carrier materials, water for injection (WFI) or water buffered with phosphate, citrate, HEPES or acetate, or Ringer or Ringer Lactate etc. being used, and the pH is typically adjusted to 5.0 to 8.0, preferably 6.5 to 7.5. The carrier or the vehicle will additionally preferably comprise salt constituents, e.g. sodium chloride, potassium chloride or other components which render the solution e.g. isotonic. Furthermore, the carrier or the vehicle can contain, in addition to the above-mentioned constituents, additional components, such as human serum albumin (HSA), polysorbate 80, sugars or amino acids.

The mode and method of administration and the dosage of the mRNA gene therapy according to the invention depend on the nature of the disease to be treated, where appropriate the stage thereof, and also the body weight, the age and the sex of the patient.

The mRNA gene therapy of the present invention may preferably be administered to the patient parenterally, e.g. intravenously, intraarterially, subcutaneously, intradermally, intra-lymph node or intramuscularly. It is also possible to administer the gene therapy mRNA topically or orally or intra-nasal. A further injection possibility is into a tumor tissue or tumor cavity (after the tumor is removed by surgery, e.g. in the case of brain tumors).

siRNA (Double Stranded RNA of Approximately 21 Residues) and Antisense (Single Stranded RNA of Approximately 21 Residues)

A benefit of the present invention is that when formulating a double stranded short interfering RNA (siRNA) or single stranded RNA, gene expression can be controlled. Mostly through specific base pairing to the target mRNA, antisense and siRNA (the antisense strand of the siRNA in the DICER complex) can block translation by (i) inducing cleavage and subsequent degradation of the mRNA and (ii) physically blocking progression of ribosomes that produce proteins while scanning the mRNA.

Antisense can also be targeted to miRNA blocking gene suppression (they can be named Antagomirs). Antisense and siRNA can be used against mRNA coding proteins responsible for inherited dominant genetic diseases (e.g. mutated keratin giving pachyonychia congenital or mutated huntingtin giving Huntington's disease), cancer disease (e.g. BCR-ABL fusion protein, mutated Ras, mutated EGFR), viral diseases (e.g. protein from HIV or HCV), degenerative diseases (e.g. BACE1 protein that gives of Alzheimer disease) or hindrance to interventions (e.g. transplantations: siRNA or antisense against key immune molecules such as chemokines involved in transplant rejection).

Examples of cancers treatable with the siRNA/antisense composition, according to the invention include malignant melanoma, all types of carcinoma (colon, renal cell, bladder, prostate, non-small cell and small cell lung carcinoma, etc.), lymphomas, sarcomas, blastomas, gliomas, etc.

Examples of infectious diseases treatable with the siRNA/antisense composition, according to the invention include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), bacterial infectious diseases, such as Legionnaire's disease (*Legionella*), gastric ulcer (*Helicobacter*), cholera (*Vibrio*), infections by *E. coli*, Staphylococci, *Salmonella* or Streptococci (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans, Histoplasma capsulatum, Coccidioides immitis, Blastomyces dermatitidis* or *Candida albicans*.

By interfering for example with IgE production or mast cell activities, the siRNA/antisense pharmaceutical composition of the present invention may prove to be useful to treat allergies as well.

The antisense RNA and at least one of the strands, preferably the sense strand of the siRNA used to formulate the siRNA/antisense formulation can ideally have a poly-G (more than 2 consecutive G residues) or a poly-U (more than 4 consecutive U residues) or a GPurine(n)G (where Purine is G or A residues and n from 1 to 4 or more) sequence(s), preferably at its end, preferably at its 3' end.

Because manufacturing of oligonucleotides by chemical synthesis is easier in very large scales (kilograms) than the enzymatic synthesis of RNA, oligoribonucleotides to use for formulating siRNA/antisense are preferably produced by chemical synthesis. The oligonucleotide can be physically linked to a moiety (chemical or biological molecule) that should penetrate inside the cells. The RNA part acts as the vehicle and the moiety as the cargo.

As used herein, the term "oligoribonucleotide" shall mean multiple ribonucleotides (i.e. a molecule comprising a ribose) linked to a phosphate group and to an organic base selected from the group consisting of cytosine (C), uracil (U) adenine (A) and guanine (G) as well as modified derivatives such as pseudouridine instead of uridine. An oligomer generally is defined to consist of a finite number of monomer units, which number ranges from a few to more than a hundred. In the context of the present invention, an oligoribonucleotide consists of about 6 to 100 ribonucleotides. Preferably, 12 to 40 and even more preferably 16 to 24.

The RNA contained in the present siRNA/antisense invention may contain chemical modifications to its subunits (e.g. on the base, or on the phosphate, or on the ribose residue) that could help manufacturing or formulation or biological activities of the siRNA/antisense (e.g. locked Nucleic Acids) or attachment to a cargo. Modifications (e.g. phosphorothioate backbone, peptide nucleic acid: PNA backbone, 2' Fluoro) described herein are also subject of the present invention. Eventually, the siRNA/antisense contains modified residues, in particular modified U and/or G residues. Thereby, the siRNA/antisense will not trigger non-specific immunomodulation through Toll Like Receptors. Hence, if desirable, the therapeutic siRNA/antisense would not trigger unwanted immunomodulation.

One or several siRNA/antisense can be combined to generate the gene interference therapy formulation according to the present invention.

The 5' end of the RNA strands can be OH, monophosphate or triphosphate, the later allowing stimulation of the cytosolic RIG-1 and enhancing immunostimulation should it synergize with the designed siRNA/antisense.

Apart from the preferential poly-G (more than 2 consecutive G residues) or poly-U (more than 4 consecutive U residues) or GPurine(n)G (where Purine is G or A residues and n from 1 to 4 or more) sequences, there is no further specific ribonucleotide sequence requirement for oligoribonucleotide molecule(s) to be suitable for preparing the siRNA/antisense composition according to the present invention. The siRNA (antisense strand)/antisense must have the capacity to bind to a precise sequence in the targeted RNAs.

In a preferred embodiment, the siRNA/antisense composition according to the invention can also be used in conjunction with another therapeutic reagent. The siRNA/antisense RNA composition of the present invention may on its own synergize with other treatments such as chemotherapeutic drugs for cancer patients or highly active anti retrovirus therapy (e.g. tri-therapy) for HIV-infected patients. Many chemotherapy regimens (gemcitabine, etopophos, cis-platin, carbo-platin, etc.) or radiotherapy protocols can be combined with an anti-cancer siRNA/antisense.

Thus, during radio/chemotherapy in cancer patients, siRNA/antisense can be used whereby the death of tumor cells can be enhanced (e.g. siRNA/antisense directed against mRNA coding for surviving factors that are important for the cancer growth or dissemination) or accompanied by the enhanced induction of indirect anti-cancer effects (e.g. immunomodulation or suppression of angiogenesis). Systemic (intra-venous or sub-cutaneous for example) as well as local (intra-tumor or intradermal or intra-lymph node for example) injections of an siRNA/antisense composition according to the present invention in patients under radio/chemotherapy may result in the treatment of the tumor, limiting its growth or dissemination.

A further embodiment is an injectible formulation comprising the siRNA/antisense RNA of the invention in combination with a pharmaceutically acceptable excipient such as Ringer Lactate.

The present invention further provides a method of using gene interference (antisense or siRNA), in particular for modulating specifically gene expression in a subject, preferably a mammal, especially a human. An effective amount of a pharmaceutical composition according to the invention is administered, optionally in combination with another therapeutic treatment (for example, radiotherapy) or agent, such as a vaccine, a cancer chemotherapy agent, an antiviral agent, anti-parasite agent or an anti-bacterial agent.

The at least one additional therapeutic agent may be administered simultaneously with the siRNA/antisense pharmaceutical composition, or the at least one additional therapeutic agent is administered sequentially with the siRNA/antisense pharmaceutical composition.

In a further embodiment, the present invention provides an ex vivo method for modifying gene expression. In one embodiment, suitable cells are isolated from the mammal, eventually differentiated and treated in vitro via administering to the cells an effective amount of a pharmaceutical siRNA/antisense composition of the present invention. The treated cells are then re-introduced into the organism. Suitable cells for such ex vivo treatment include tumor-specific cytotoxic T-cells treated with siRNA/antisense blocking CTLA-4, thus reducing death in those therapeutic cells adoptively transferred into tumor patients.

The siRNA/antisense composition of the invention comprises, in addition to antisense and/or siRNA and salts, and other therapeutic agents (eventually attached to the RNA), a pharmaceutically acceptable carrier and/or a pharmaceutically acceptable vehicle and/or pharmaceutically acceptable diluent. Appropriate routes for suitable formulation and preparation of the siRNA/antisense agent according to the invention and the vaccine are disclosed in Remington: "The Science and Practice of Pharmacy," 20th Edn., A. R. Gennaro, Editor, Mack Publishing Co., Easton, Pa. (2003). Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers. The particular embodiments of the siRNA/antisense agent are chosen according to the physical properties, for example in respect of solubility, stability, bioavailability or degradability. Controlled or constant release of the active drug (-like) components according to the invention includes formulations based on lipophilic depots (e.g. fatty acids, waxes or oils). Preferred carriers are typically aqueous carrier materials, water for injection (WFI) or water buffered with phosphate, citrate, HEPES or acetate, or Ringer or Ringer Lactate etc. being used, and the pH is typically adjusted to 5.0 to 8.0, preferably 6.5 to 7.5. The carrier or the vehicle will additionally preferably comprise salt constituents, e.g. sodium chloride, potassium chloride or other components which render the solution e.g. isotonic. Furthermore, the carrier or the vehicle can contain, in addition to the abovementioned constituents, additional components, such as human serum albumin (HSA), polysorbate 80, sugars or amino acids.

The mode and method of administration and the dosage of the siRNA/antisense agent according to the invention depend on the nature of the disease to be treated, where appropriate the stage thereof and also the body weight, the age and the sex of the patient.

The siRNA/antisense composition of the present invention may preferably be administered to the patient parenterally, e.g. intravenously, intraarterially, subcutaneously, intradermally, intra-lymph node or intramuscularly. It is also possible to administer the siRNA/antisense agent topically, intra-nasal or orally. A further injection possibility is into a tumor tissue or tumor cavity (after the tumor is removed by surgery, e.g. in the case of brain tumors).

The siRNA/antisense composition of the present invention may be used or administered in combination with compounds that allow redistribution of molecules within cells such as endosome destabilization compounds that trigger the release of contents into the cytosole (e.g. histidine-based systems for pH-responsive endosomal escape, polycations with intrinsic endosomolytic activity by the proton sponge mechanism, Chloroquine or fusogenic peptides such as peptide HA24 from influenza virus hemagglutinin)

EXAMPLES

The following examples are intended to illustrate preferred embodiments of the invention and should not be interpreted to limit the scope of the invention as defined in the claims.

Method for the Preparation of an Immunostimulatory RNA Composition

An oligoribonucleotide of 21 residues and having the sequence: 5' AGUGUUAUCUUGUAUGGGGGG 3' (SEQ ID NO: 1) is chemically synthesized and purified by reverse phase HPLC. The product is then precipitated using sodium chloride and ethanol, resuspended at 1 mg/ml in pure water, lyophilized and resuspended at 5 mg/ml in pure water. It is then further diluted to 0.5 mg/ml final using Ringer Lactate. The formulation is left for a few minutes on the bench and can then be eventually further diluted with injection solution (for example Ringer lactate or saline).

Method for the Preparation of an Antisense RNA Composition

An oligoribonucleotide of 23 residues and having the sequence: 5' CAUUUCCGAUAAGGCUUGGGGGG 3' (antisense to IL-10-coding Mrna; U residues are locked nucleic acids whereby the ribose contains a bridge from the 2' oxygen to the 4' carbon) (SEQ ID NO: 2) is chemically synthesized and purified by reverse phase HPLC. The product is then precipitated using sodium chloride and ethanol, resuspended at 1 mg/ml in pure water, lyophilized and resuspended at 5 mg/ml in pure water. It is then further diluted to 0.5 mg/ml final using Ringer Lactate. The formulation is left for a few minutes on the bench and can then be eventually further diluted with injection solution (for example Ringer lactate or saline).

Method for the Preparation of an siRNA Composition

Two oligoribonucleotides having the sequence: sense strand: 5' CCCAAAUUACGUGUACUACGGGGGG 3' (SEQ ID NO: 3); antisense strand: 5' GUAGUA-CACGUAAUUUGGG 3' (targeting CTLA-4-coding mRNA [18], U residues are locked nucleic acids whereby the ribose contains a bridge connecting the 2' oxygen and 4' carbon) (SEQ ID NO: 4) are chemically synthesized and purified by reverse phase HPLC. The two RNA products are then precipitated using sodium chloride and ethanol, resuspended at 1 mg/ml in pure water, mixed together at equal amount, heated up to 80° C., cooled down slowly to allow specific hybridization of the antisense and sense strands, lyophilized and resuspended at 5 mg/ml in pure water. The siRNA is then further diluted to 0.5 mg/ml final using Ringer lactate. The formulation is left for a few minutes on the bench and can then be eventually further diluted with injection solution (for example Ringer lactate or saline).

Method for the Preparation of an mRNA Composition A mRNA of 818 residues coding for the protein NY-ESO-1 and having the sequence 5' CAP-ATCCTCGTGG GCCCTGACCT TCTCTCTGAG AGCCGGGCAG AGGCTCCGGA GCCATGCAGG CCGAAGGCCG GGGCACAGGG GGTTCGACGG GCGATGCTGA TGGCCCAGGA GGCCCTGGCA TTCCTGATGG CCCAGGGGGC AATGCTGGCG GCCCAGGAGA GGCGGGTGCC ACGGGCGGCA GAGGTCCCCG GGGCGCAGGG GCAGCAAGGG CCTCGGGGCC GGGAGGAGGC GCCCCGCGGG GTCCGCATGG CGGCGCGGCT TCAGGGCTGA ATGGATGCTG CAGATGCGGG GCCAGGGGGC CGGAGAGCCG CCTGCTTGAG TTCTACCTCG CCATGCCTTT CGCGACACCC ATGGAAGCAG AGCTGGCCCG CAGGAGCCTG GCCCAGGATG CCCCACCGCT TCCCGTGCCA GGGGTGCTTC TGAAGGAGTT CACTGTGTCC GGCAACATAC TGACTATCCG ACTGACTGCT GCAGACCACC GCCAACTGCA GCTCTCCATC AGCTCCTGTC TCCAGCAGCT TTCCCTGTTG ATGTGGATCA CGCAGTGCTT TCTGCCCGTG TTTTTGGCTC AGCCTCCCTC AGGGCAGAGG CGCTAAGCCC AGCCTGGCGC CCCTTCCTAG GTCATGCCTC CTCCCCTAGG GAATGGTCCC AGCACGAGTG GCCAGTTCAT TGTGGGGGCC TGATTGTTTG TCGCTGGAGG AGGACGGCTT ACATGTTTGT TTCTGTAGAA AATAAAACTG AGCTACGAAA AAAAAAAAAA AAAAAAAAAA AAAAAAAAAA AAAAAAAAAA AAAAAAAAAA AAAAAAAAAA GGGGGG 3' (where CAP is 7-methylguanosine cap, bold ATG is the start codon, underlined TAA is the stop codon) (SEQ ID NO: 5) is biologically synthesized (transcription of a template plasmid using T7 RNA polymerase) and purified. The mRNA product is then precipitated using sodium chloride and ethanol, resuspended at 1 mg/ml in pure water, lyophilized and resuspended at 5 mg/ml in pure water. The mRNA is then further diluted to 0.5 mg/ml final using Ringer lactate. The formulation is left for a few minutes on the bench and can then be eventually further diluted with injection solution (for example Ringer lactate or saline).

Figure 1B:
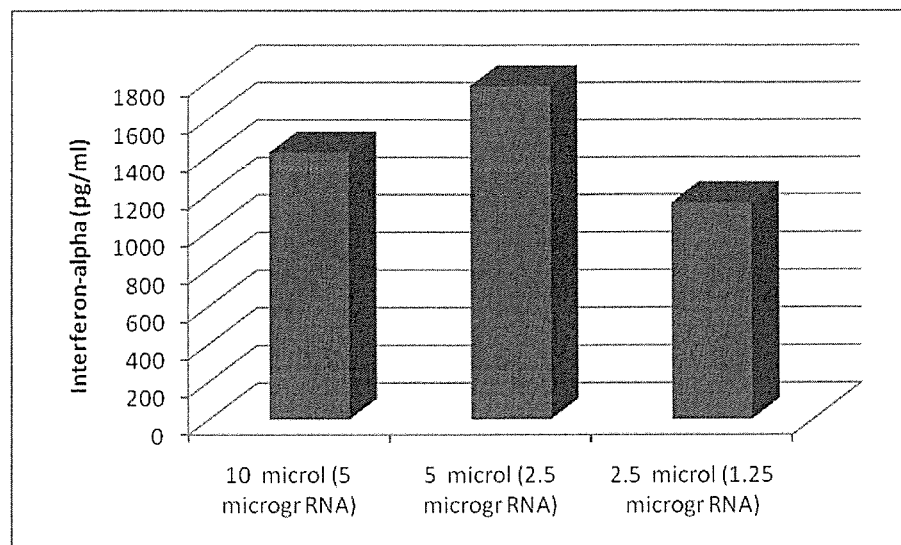

FIGS. 1A and 1B show that RNA formulated in Ringer Lactate is biologically active when sodium is the counter ion of the RNA.

In A, the 21 mere (or 21 nucleotides or 21 residues) RNA oligonucleotide (5' AGUGUUAUCUUGUAUGGGGGG 3', (SEQ ID NO: 1) was obtained either "Desalted" ("21GD": eluted after chemical synthesis, precipitated with sodium acetate and ethanol, resuspended in water and lyophilized by freeze-drying) or "HPLC purified" ("21GHPLC": eluted after synthesis, run on a reverse phase chromatography using TEA-buffers, collected, dried, resuspended in water and lyophilized by freeze drying) or "HPLC purified" and precipitated with sodium acetate and lyophilized ("21GH-PLC-NaAc-Lyo": eluted after synthesis, run on a reverse phase chromatography using TEA-buffers, collected, dried, resuspended in water, precipitated using sodium acetate/ ethanol and lyophilized by freeze drying). In all cases, 1 microliter of RNA (5 micrograms) was put in a well from a tissue culture 96 well plate and diluted with 9 microliters of Ringer lactate. PBMCs from healthy humans were prepared using Ficoll® gradient separation. They were then washed with PBS and resuspended at 5 million per ml in RPMI with 10% fetal calf serum plus penicillin and streptomycin. Two hundred microliters (1 million of cells) were added to the formulated RNA in the well of the 96 well plate. These preparations were incubated for 24 hours at 37° C. with 5% CO2. PBMCs cultured alone (in the absence of formulated RNA) were used as controls. Then, the supernatants of the culture were collected and eventually frozen at –20° C. The contents of IFN-alpha in these supernatants were evaluated using 20 microliters of supernatants and ELISA kits from Bender (IFN-alpha). The results are presented in pg/ml in the cell culture supernatant. They demonstrate that while the desalted RNA forms biologically active complexes when formulated in Ringer Lactate (21GD) at room temperature before addition of human PBMCs (1 million cells in 200 microliters complete medium), the HPLC purified RNA ("21GHPLC") does not, as can be seen when measuring the content of interferon-alpha in supernatants of 24 hours cultures. However, the same HPLC purified RNA is biologically active when formulated in Ringer Lactate as long as it is, before formulation, precipitated with Sodium Acetate/Ethanol, dried, resuspended in water and lyophilized by freeze drying. This RNA ("21GHPLC-NaAc-Lyo) has sodium as counter ion while the untreated HPLC purified RNA ("21GHPLC") has triethylamine as counter ion. PBMCs alone do not produce any detectable interferon-alpha. Thus, this figure shows that poly-G containing RNA forms biologically active (penetrating) complexes when the counter ion of the RNA is set to sodium. When the RNA has as counter ion triethylamine ("21GHPLC"), it fails to become biologically active after addition of a calcium-containing solution. In B, the titration of poly-G-containing "desalted" RNA (21GD: 5' AGUGUUAUCUU-GUAUGGGGGG 3' (SEQ ID NO: 1)) formulated in Ringer Lactate shows that strong biological activity is seen even with final concentrations of RNA of 1.25 micrograms in 200 microliters of culture (6.25 micrograms formulated RNA/ ml).

Figure 2A:
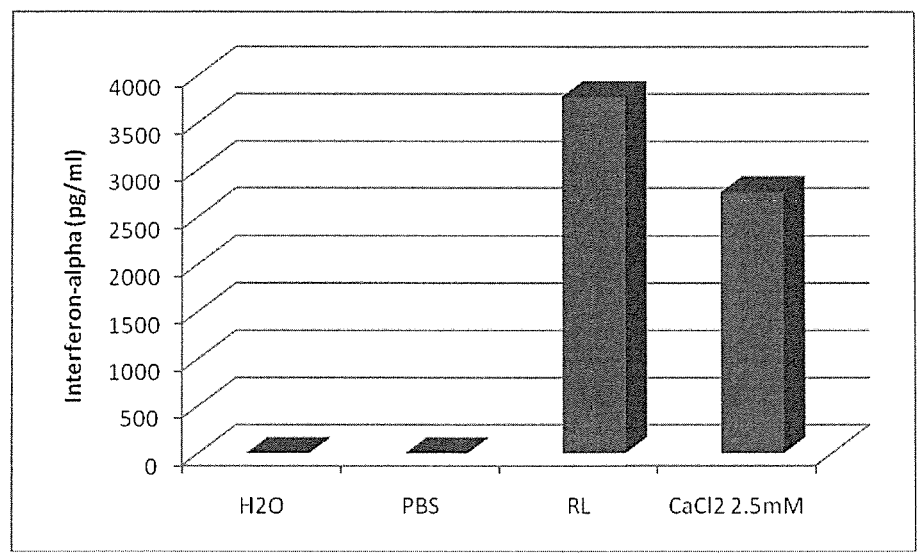
FIGS. 2A and 2B show the biological activity (immunostimulation) of an RNA diluted in calcium containing solutions.
Figure 2B:
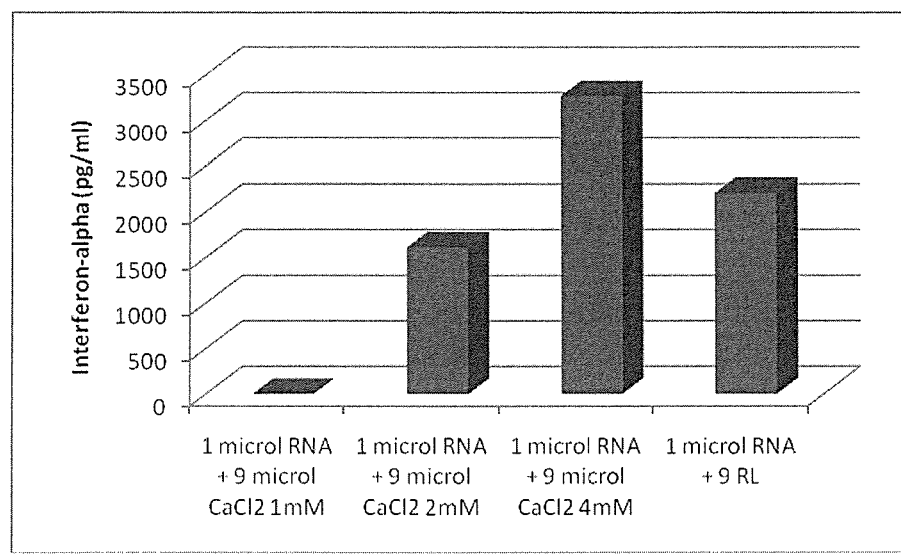

FIGS. 2A and 2B show the biological activity (immunostimulation) of an RNA diluted in calcium containing solutions. In A, the "Desalted" (no HPLC purification) 21 mer RNA oligonucleotide (21GD: 5' AGUGUUAUCUU-GUAUGGGGG 3' (SEQ ID NO: 1); counter ion is sodium; stock solution at 5 mg/ml in water) was formulated at 0.5 mg/ml in pure water (H2O), or in Phosphate Buffer Saline (PBS: 8 g NaCl+0.2 g KCl+1.44 g Na2HPO4+0.24 g KH2PO4 in 1l water, adjusted to pH 7.4) or in Ringer lactate (RL) or in Calcium solution at 2.5 mM (CaCl$_2$ 2.5 mM). In all cases presented in A, 1 microliter of RNA (5 micrograms) was put in a well from a cell culture 96 well plate and diluted with 9 microliters of the indicated water or salt solution. PBMCs from healthy humans were prepared using Ficoll® gradient separation. They were then washed with PBS and resuspended at 5 millions per ml in RPMI with 10% fetal calf serum plus penicillin and streptomycin. Two hundred microliters (1 million of cells) were added to the formulated RNA in the well of the 96 well plate. These preparations were incubated for 24 hours at 37° C. with 5% CO2. Then, the supernatants of the culture were collected and eventually frozen at –20° C. The contents of IFN-alpha in these supernatants were evaluated using 20 microliters of supernatants and ELISA kits from Bender (IFN-alpha). The results are presented in pg/ml in the cell culture supernatant. They demonstrate that RNA can show biological activity, thus penetrate cells, only when it is formulated in Calcium containing solutions (Ringer lactate or Calcium Chloride solutions). Cations present in PBS (sodium and potassium) did not allow to turn the RNA in a biologically active (penetrating) molecule. In B, the formulation of RNA (5 micrograms of RNA in 1 microliter on which is added 9 microliters of solution) in Calcium containing-solutions (1 mM, 2 mM or 4 mM CaCl2 solutions) shows that more than 1 mM of CaCl2 is needed in order to generate biologically active RNA complexes.

Figure 3A:
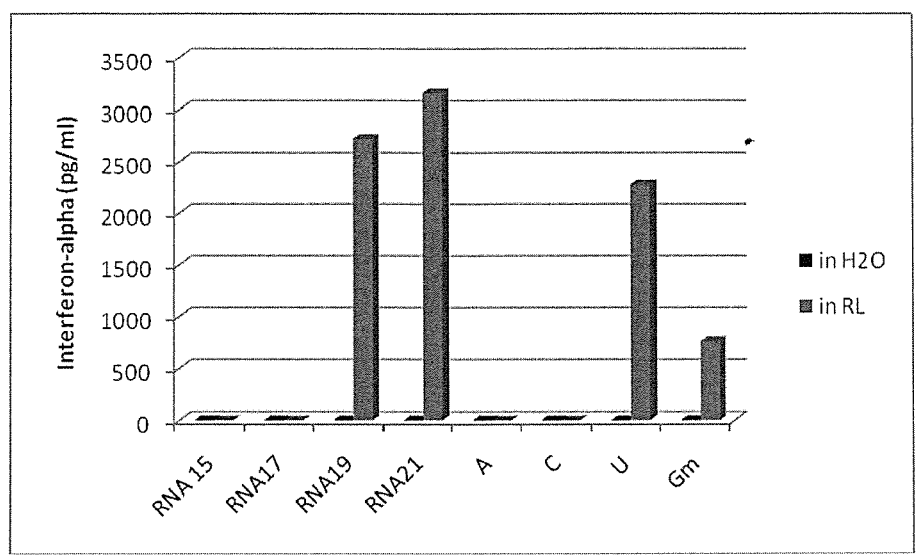
FIGS. 3A and 3B show several RNA oligonucleotides formulated to have sodium as counter ion and diluted in calcium-containing solution were cultured with human immune cells.
Figure 3B:
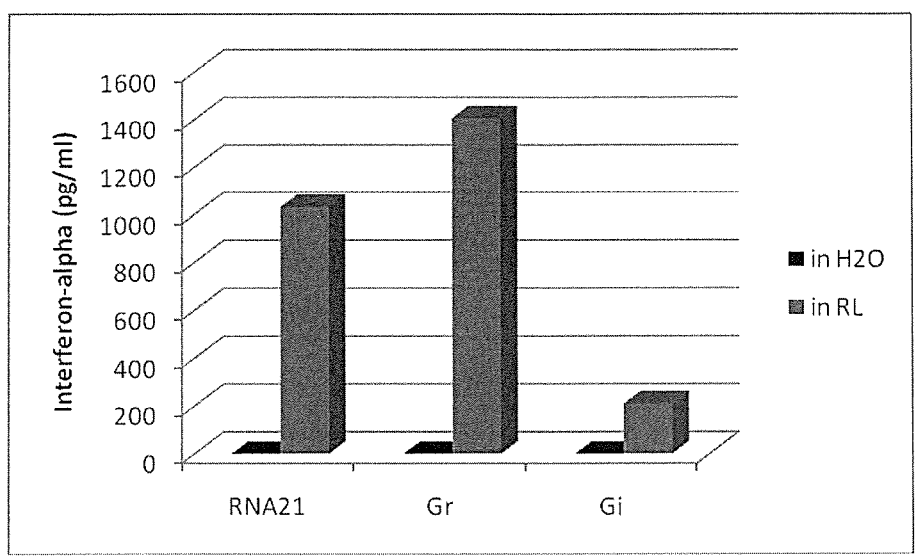

FIGS. 3A and 3B show several RNA oligonucleotides formulated to have sodium as counter ion and diluted in calcium-containing solution were cultured with human immune cells. Sequences in A: RNA 15: 5' AGU GUU AUC UUG UAU 3' (SEQ ID NO: 6); RNA17: 5' AGU GUU AUC UUG UAU GG 3' (SEQ ID NO: 7); RNA 19: 5' AGU GUU AUC UUG UAU GGG G 3' (SEQ ID NO: 8); RNA 21: 5' AGU GUU AUC UUG UAU GGG GGG 3' (SEQ ID NO: 1); A: 5' AGU GUU AUC UUG UAU AAA AAA 3' (SEQ ID NO: 9); C: 5' AGU GUU AUC UUG UAU CCC CCC 3' (SEQ ID NO: 10); U: 5' AGU GUU AUC UUG UAU UUU UUU 3' (SEQ ID NO: 11); Gm: 5' AGU GUU AGG GGG GUC UUG UAU 3' (SEQ ID NO: 12). Sequences in B: RNA 21: 5' AGU GUU AUC UUG UAU GGG GGG3' (SEQ ID NO: 1); Gr: 5' GGG GGG AGU GUU AUC UUG UAU 3' (SEQ ID NO: 13); Gi: 5' AGU GUU AUC UUG UAU GGA AGG 3' (SEQ ID NO: 14). The biological activity of the RNA is detected by measuring interferon-alpha (INF-alpha) in the culture supernatants. For each RNA, a stock solution at 5 mg/ml in water was formulated at 0.5 mg/ml in water (H2O) or Ringer Lactate (RL). In all cases presented, 1 microliter of RNA (5 micrograms) was put in a well from a cell culture 96 well plate and diluted with 9 microliters of water or RL. PBMCs from healthy humans were prepared using Ficoll® gradient separation. They were then washed with PBS and resuspended at 5 millions per ml in RPMI with 10% fetal calf serum plus penicillin and streptomycin. Two hundred microliters (1 million of cells) were added to the formulated RNA in the well of the 96 well plate. These preparations were incubated for 24 hours at 37° C. with 5% CO2. Then, the supernatants of the culture were collected and eventually frozen at –20° C. The contents of IFN-alpha in these supernatants were evaluated using 20 microliters of supernatants and ELISA kits from Bender. The results are presented in pg/ml in the cell culture supernatant. They demonstrate that RNA can show biological activity, thus penetrate cells, only when it is in Ringer lactate (presence of calcium) and contains certain sequences such as for example a poly-G (more than 2 consecutive G residues) or a poly-U (more than 4 consecutive U residues) or a GPurine$_{(n)}$G (where Purine is G or A residues and n from 1 to 4 or more) sequence. Those sequences are known to allow the formation of tetrads. This sequence listing is not exhaustive and other sequences may help turning RNA into biologically active cell penetrating molecules when they have sodium as counter ion and formulated in calcium containing solutions.

FIG. 4 depicts the possible sequence or structure of (A) isRNA or antisense RNA, (B) siRNA (N stands for ribonucleotide or modified ribonucleotide or deoxyribonucleotide) and (C) mRNA ("(A)" means more than 10 A residues) according to the invention.

Figure 5A:
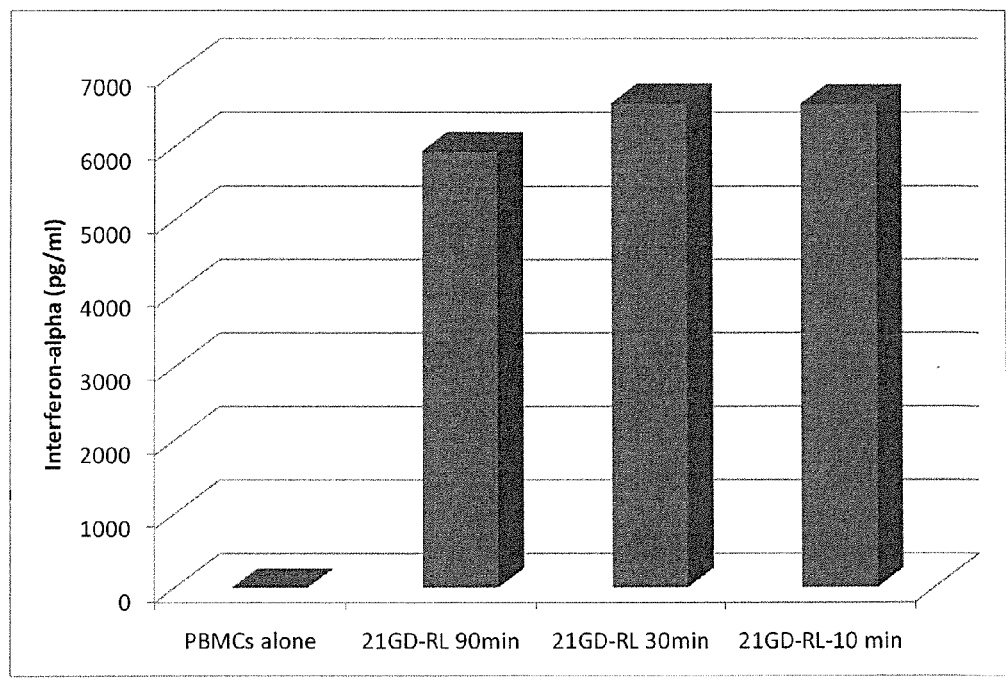
FIGS. 5A and 5B show that formulated RNA is stable.
Figure 5B:
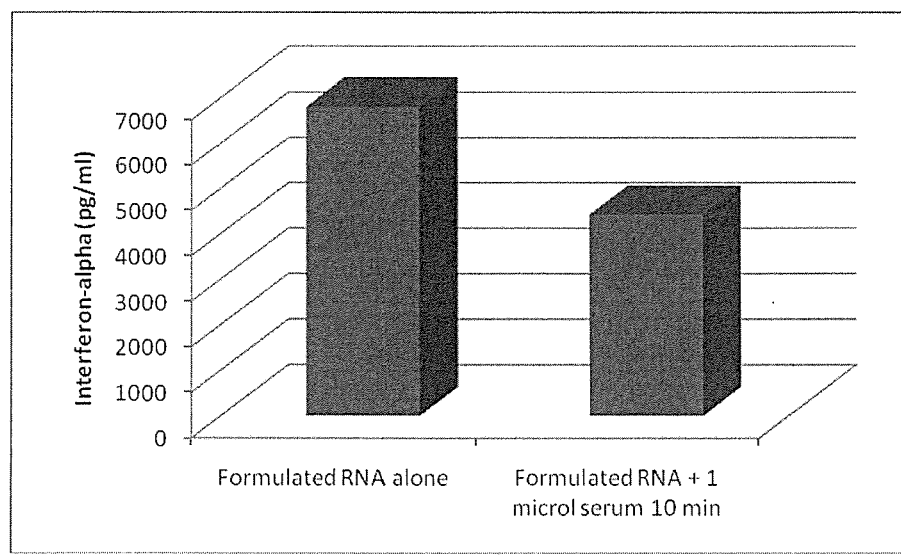

FIGS. 5A and 5B Shows that Formulated RNA is Stable

In A, RNA (21GD: desalted RNA oligonucleotide with the sequence 5' AGUGUUAUCUUGUAUGGGGGG 3', SEQ ID NO: 1) was formulated as above (5 micrograms of RNA in one microliter on which 9 microliters of Ringer lactate (RL) are added) and incubated 10 minutes (21GD-RL-10 min) or 30 min (21GD-RL-30 min) or 90 min(21GD-RL-90 min) at room temperature before the addition of human PBMCs (prepared as written above). PBMCs alone are used as negative control. Interferon-alpha measurement in the 24 hours culture supernatant indicate that RNA formulated in RL is stable at room temperature for at least 90 min and biologically active (penetrating cells).

It is known that unprotected RNA is quickly degraded by ubiquitous RNases. In B, RNA (21GHPLC-Na-Ac-lyo: HPLC purified RNA oligonucleotide 5' AGUGUUAUCUU-GUAUGGGGGG 3' (SEQ ID NO: 1) treated to have sodium as counter ion) was formulated as above (5 micrograms of RNA in one microliter on which 9 microliters of Ringer lactate are added). Eventually ("Formulated RNA+1 microl serum 10 min"), 1 microliter of fresh human serum was added in the 10 microliters of formulated RNA and left 10 min at room temperature before the addition of 200 microliters of complete medium containing PBMCs from healthy human. As control (Formulated RNA alone), the 10 microliters of formulated RNA were left at room temperature during the same time as the serum-treated counterpart, before addition of the PBMCs. The results show that in those RNase-contaminated conditions, the half life of the formulated RNA is of more than 10 minutes. Thus, formulated RNA could be injected in mammals for treatment as its degradation by natural RNase, that reduce its bioavailability, is slow. However, modifications on the bases that would retard degradation by RNases could increase the biological activity.

Figure 6B:
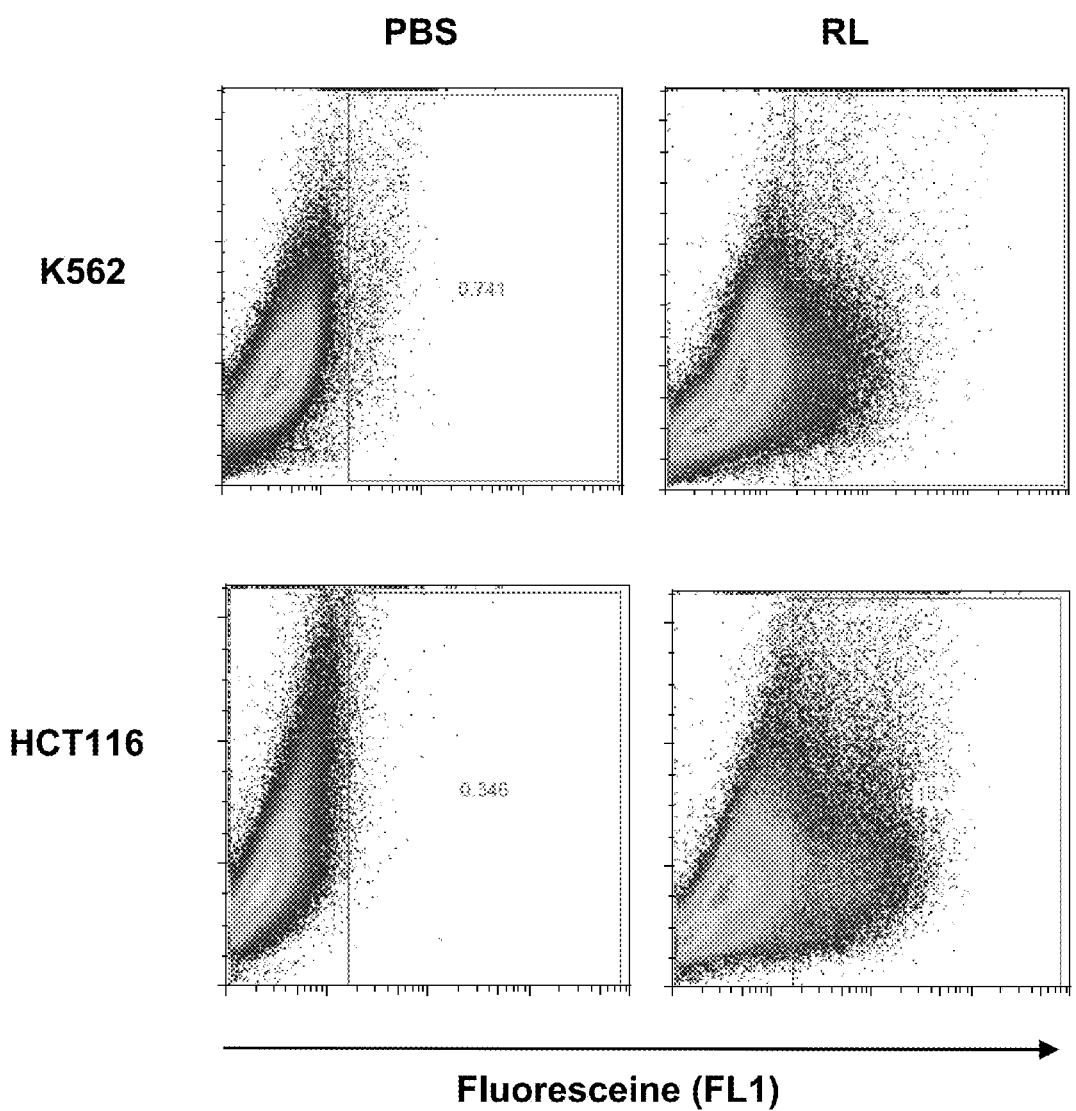

FIGS. 6A and 6B Show that Cells Take Up Fluorescent RNA

In A, RNA (Fluo 6S: desalted RNA oligonucleotide with the sequence 5' Fluorescein-AUA UUC UUG UAU GGG GGG 3' (SEQ ID NO: 15)) was formulated as above (5 micrograms of desalted RNA in one microliter on which 9 microliters of PBS or Ringer lactate (RL) are added) and incubated 5 minutes. PBMCs from healthy humans were prepared using Ficoll® gradient separation. They were then washed with PBS and resuspended at 5 million per ml in OptiMEM (serum-free medium).

2 microliters of RNA preparations (1 microgram) are put in a well of a 96 well plate. Two hundred microliters (1 million of cells) were added to the formulated RNA in the well of the 96 well plate. These preparations were incubated for 4 to 6 hours at 37° C. with 5% CO2. Then 10 microliters of CD14 antibody (BD-Pharmingen) are added in each well. Cells are incubated 30 minutes at 4° C. Then, cells are washed twice with PBS by centrifugating 5 minutes at 1500 rpm, discarding the supernatants (free fluorescent oligonucleotide and free antibody) and adding 200 microliters of fresh PBS. Thereafter cells are analysed by FACS. Numbers indicate the percentage of cells in each quadrant. "PBMCs" are cells incubated without fluorescent RNA. "PBS" are cells incubated with the fluorescent RNA formulated in PBS. "RL" are cells incubated with the fluorescent RNA formulated in Ringer Lactate. "Rottlerin" are cells incubated with the fluorescent RNA formulated in Ringer Lactate and in the presence of 3.3 micromolar Rottlerin (an inhibitor of endocytosis, most specifically macropinocytosis). "Chloroquine" are cells incubated with the fluorescent RNA formulated in Ringer Lactate and in the presence of 5 micrograms per ml of Chloroquine (an inhibitor of endosomes acidification). "Formaldehyde" are cells incubated with the fluorescent RNA formulated in Ringer Lactate after having been fixed by 10 minutes incubation in PBS containing 1% formaldehyde and 2 washes in PBS. "Lipofectamine alone" are cells incubated with two microliters of lipofectamine (Invitrogen) alone. "Fluo 6S in Lipofectamine alone" are cells incubated with the fluorescent RNA formulated in Lipofectamine as recommended by the manufacturer. The results show that when formulated in Ringer Lactate, the fluorescent oligonucleotide penetrates in cells, mostly in phagocytic cells (CD14 positive) including myeloid suppressor cells (e.g. IL2-R-positive cells from cancer patients, data not shown). Because Rottlerin reduces the uptake (9.45% fluorescein positive cells without inhibitor versus 2.7% in Rottlerin fixed cells), the phenomenon is partly due to micropinocytosis. Chloroquine does not affect the uptake. However, penetration of RNA is observed in formaldehyde fixed cells and in cells kept bellow 10° C. (data not shown). Thus, a spontaneous uptake independent of cell activities is possible. The uptake of desalted (sodium as counter ion) RNA formulated in Ringer Lactate (calcium) is higher than the one observed using a standard transfection formulation such as Lipofectamin (less than 7% fluorescein positive cells using Lipofectamin encapsulated fluorescent RNA). It was further observed that uptake of RNA having sodium as counter ion and formulated in Ringer Lactate is higher when the experiment is made in serum-free medium (RPMI or as it is here the case, OptiMEM) than when made in complete medium containing serum. Thus, optimal uptake is seen when low RNase activities are present. This suggests that for use in vivo, the RNA could ideally be made (sequence optimization and adequate modifications) to resist RNase. The present experiment further documents the capacity of the formulated RNA to bring a cargo (here fluorescein) inside cells. In B, RNA (Fluo 6S: desalted RNA oligonucleotide with the sequence 5' Fluorescein-AUA UUC UUG UAU GGG GGG 3' (SEQ ID NO: 15)) was formulated as above (5 micrograms of desalted RNA in one microliter on which 9 microliters of PBS or Ringer lactate (RL) are added) and incubated 5 minutes. The human cell lines K562 (myelogenous leukemia) and HCT116 (colorectal carcinoma) were prepared at 5 million per ml. 200 microliters of cells were added on top of 2 microliters (1 microgram) of formulated RNA. Cells were incubated 4 to 6 hours at 37° C. with 5% CO2. Then, cells are washed twice with PBS by centrifugating 5 minutes at 1200 rpm, discarding the supernatants (free fluorescent oligonucleotide) and adding 200 microliters of fresh PBS. Thereafter cells are analysed by FACS. The numbers indicate the percentage of cells in the gate. The results demonstrate that the desalted (sodium as counter ion) fluorescent RNA formulated in Ringer lactate (Calcium) penetrates tumor cells. 8.4% (K562) or 18% (HCT) cells have detectable amounts of fluorescent RNA after the 4 to 6 hours incubation period. It was further observed that uptake is higher when the experiment is made in serum-free medium (RPMI or as it is here the case, OptiMEM) than when made in complete medium containing serum. Thus, optimal uptake is seen when low RNase activities are present. This suggests that for use in vivo, the RNA could ideally be made (sequence optimization and adequate modifications) to resist Rnase. The present experiment further documents the capacity of the formulated RNA to bring a cargo (here fluorescein) inside tumor cells.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. Furthermore, the teachings and disclosures of all references cited herein are expressly incorporated in their entireties by reference.

REFERENCES

[1] Wolff J A, Malone R W, Williams P, Chong W, Acsadi G, Jani A, et al. Direct gene transfer into mouse muscle in vivo. Science 1990 Mar. 23; 247 (4949 Pt 1): 1465-8.

[2] Hoerr I, Obst R, Rammensee H G, Jung G. In vivo application of RNA leads to induction of specific cytotoxic T lymphocytes and antibodies. Eur J Immunol 2000 January; 30(1):1-7.

[3] Diebold S S, Kaisho T, Hemmi H, Akira S, Reis e Sousa C. Innate antiviral responses by means of TLR7-mediated recognition of single-stranded RNA. Science 2004 Mar. 5; 303(5663):1529-31.

[4] Heil F, Hemmi H, Hochrein H, Ampenberger F, Kirschning C, Akira S, et al. Species-specific recognition of single-stranded RNA via toll-like receptor 7 and 8. Science 2004 Mar. 5; 303(5663):1526-9.

[5] Ozpolat B, Sood A K, Lopez-Berestein G. Nanomedicine based approaches for the delivery of siRNA in cancer. J Intern Med January; 267(1):44-53.

[6] Jarrossay D, Napolitani G, Colonna M, Sallusto F, Lanzavecchia A. Specialization and complementarity in microbial molecule recognition by human myeloid and plasmacytoid dendritic cells. Eur J Immunol 2001 November; 31(11):3388-93.

[7] Panter G, Kuznik A, Jerala R. Therapeutic applications of nucleic acids as ligands for Toll-like receptors. Curr Opin Mol Ther 2009 April; 11(2):133-45.

[8] Scheel B, Braedel S, Probst J, Carralot J P, Wagner H, Schild H, et al. Immunostimulating capacities of stabilized RNA molecules. Eur J Immunol 2004 February; 34(2):537-47.

[9] Bourquin C, Schmidt L, Hornung V, Wurzenberger C, Anz D, Sandholzer N, et al. Immunostimulatory RNA oligonucleotides trigger an antigen-specific cytotoxic T-cell and IgG2a response. Blood 2007 Apr. 1; 109(7): 2953-60.

[10] Diebold S S, Massacrier C, Akira S, Paturel C, Morel Y, Reis e Sousa C. Nucleic acid agonists for Toll-like receptor 7 are defined by the presence of uridine ribonucleotides. Eur J Immunol 2006 December; 36(12): 3256-67.

[11] Pascolo S. Vaccination with messenger RNA. Methods Mol Med 2006; 127:23-40.

[12] Probst J, Weide B, Scheel B, Pichler B J, Hoerr I, Rammensee H G, et al. Spontaneous cellular uptake of exogenous messenger RNA in vivo is nucleic acid-specific, saturable and ion dependent. Gene Ther 2007 August; 14(15): 1175-80.

[13] Jing N, De Clercq E, Rando R F, Pallansch L, Lackman-Smith C, Lee S, et al. Stability-activity relationships of a family of G-tetrad forming oligonucleotides as potent HIV inhibitors. A basis for anti-HIV drug design. J Biol Chem 2000 Feb. 4; 275(5):3421-30.

[14] Xu Y, Ishizuka T, Kimura T, Komiyama M. A U-tetrad stabilizes human telomeric RNA G-quadruplex structure. J Am Chem Soc June 2; 132(21):7231-3.

[15] Pan B, Shi K, Sundaralingam M. Synthesis, Purification and Crystallization of Guanine-rich RNA Oligonucleotides. Biol Proced Online 2004; 6:257-62.

[16] Kerkmann M, Costa L T, Richter C, Rothenfusser S, Battiany J, Hornung V, et al. Spontaneous formation of nucleic acid-based nanoparticles is responsible for high interferon-alpha induction by CpG-A in plasmacytoid dendritic cells. J Biol Chem 2005 Mar. 4; 280(9):8086-93.

[17] Pasquali S, Mocellin S. The anticancer face of interferon alpha (IFN-alpha): from biology to clinical results, with a focus on melanoma. Curr Med Chem; 17(29): 3327-36.

[18] Yu Y, Wu H, Tang Z, Zang G. CTLA4 silencing with siRNA promotes deviation of 50 Th1/Th2 in chronic hepatitis B patients. Cell Mol Immunol 2009 April; 6(2): 123-7.

The invention claimed is:

1. A composition comprising:
   a complex of RNA and an alkali metal counter ion, the RNA having a sequence containing four consecutive G residues consisting of 5'-AGUGUUAUCUUGUAUGGGG-3' (SEQ ID NO: 8); and
   a dication-containing solution.

2. The composition of claim 1 wherein the dication is an alkaline earth metal.

3. The composition of claim 2 wherein the alkaline earth metal is calcium.

4. The composition of claim 1 wherein the alkali metal is sodium.

5. The composition of claim 1 wherein the RNA consists of unmodified nucleotide residues.

6. The composition of claim 1 wherein the RNA contains one or more modified nucleotide residues.

7. The composition of claim 1 wherein the RNA is linked to a chemical or biological cargo entity.

8. The composition of claim 1 together with a pharmaceutically acceptable excipient.

9. A method for stimulating a host immune response in a subject, comprising the step of administering to the subject an effective amount of a pharmaceutical composition comprising a complex of RNA, the RNA having a sequence consisting of 5'-AGUGUUAUCUUGUAUGGGG-3' (SEQ ID NO: 8), and a sodium counter ion in a calcium-containing solution.

10. The method of claim 9 wherein the subject is a mammal.

11. The method of claim 10 wherein the mammal is a human.

12. The method of claim 9 wherein the composition induces production of interferon-α in the subject.

13. A method for stimulation of the production of interferon-α in human immune cells in vitro, comprising administering to human immune cells in vitro an effective amount of a pharmaceutical composition comprising a complex of RNA, the RNA having a sequence consisting of 5'-AGUGUUAUCUUGUAUGGGG-3' (SEQ ID NO: 8), and a sodium counter ion in a calcium-containing solution.

14. A method for the preparation of a composition comprising a complex of RNA with an alkali metal as counter ion in a dication-containing solution comprising the steps of:
   (a) providing a RNA having a sequence consisting of 5'-AGUGUUAUCUUGUAUGGGG-3' (SEQ ID NO: 8);
   (b) next, preparing a RNA-alkali metal complex of the RNA having a sequence consisting of 5'-AGUGUUAUCUUGUAUGGGG-3' (SEQ ID NO: 8) and an alkali metal counter ion; and
   (c) then, adding a dication to the RNA-alkali metal complex.

15. The method of claim 14 wherein the step of preparing the RNA-alkali metal complex comprises ion exchange or precipitation.

16. The method of claim 15 wherein the step of preparing the RNA-alkali metal complex comprises precipitation of the RNA-alkali metal complex in a mixture of a sodium salt and an alcohol.

17. The method of claim 15, wherein the step of preparing the RNA-alkali metal complex comprises precipitation of the RNA-alkali metal complex in a mixture of sodium chloride or sodium acetate, and ethanol.

18. The method of claim 14, wherein the dication is calcium, and the composition comprising a complex of RNA with an alkali metal as counter ion in a dication-containing solution is an aqueous solution containing 0.2 to 20 mM calcium.

19. The method of claim 18 wherein an aqueous solution of 1 to 20 mM $CaCl_2$ to an aqueous solution of 1 to 10 mg/ml of the RNA-alkali metal complex the composition comprising a complex of RNA with an alkali metal as counter ion in a dication-containing solution has a final concentration of 0.2 to 20 mM $Ca^{2+}$.

20. A composition comprising:
   a complex of RNA and an alkali metal counter ion, the RNA having a sequence selected from the group consisting of:

5'-AGUGUUAUCUUGUAUGGGGG-3', (SEQ ID NO: 1)

5'-AGUGUUAUCUUGUAUGGGG-3', (SEQ ID NO: 8)

5'-AGUGUUAUCUUGUAUUUUUUU-3', (SEQ ID NO: 11)

5'-AGUGUUAGGGGGGUCUUGUAU-3', (SEQ ID NO: 12)

5'-GGGGGGAGUGUUAUCUUGUAU-3', (SEQ ID NO: 13)

5'-AGUGUUAUCUUGUAUGGAAGG-3', (SEQ ID NO: 14)
and

5'-AUA UUC UUG UAU GGG GGG-3'; (SEQ ID NO: 15)
and a dication-containing solution.

21. The composition of claim 20 wherein the dication is an alkaline earth metal.

22. The composition of claim 21 wherein the alkaline earth metal is calcium.

23. The composition of claim 20 wherein the alkali metal is sodium.

24. The composition of claim 20 wherein the RNA is linked to a chemical or biological cargo entity.

25. A composition comprising:

a complex of RNA and an alkali metal counter ion, the RNA having a sequence selected from the group consisting of:

5'-AGUGUUAUCUUGUAUGGGGGG-3' (SEQ ID NO: 1),

5'-AGUGUUAGGGGGGUCUUGUAU-3' (SEQ ID NO: 12),

5'-GGGGGGAGUGUUAUCUUGUAU-3' (SEQ ID NO: 13), and

5'-AUA UUC UUG UAU GGG GGG-3' (SEQ ID NO: 15); and a dication-containing solution.

26. The composition of claim 25 wherein the dication is an alkaline earth metal.

27. The composition of claim 25 wherein the alkaline earth metal is calcium.

28. The composition of claim 25 wherein the alkali metal is sodium.

29. The composition of claim 25 wherein the RNA is linked to a chemical or biological cargo entity.

* * * * *

SEQUENCE LISTING

```
<160> NUMBER OF SEQ ID NOS: 15

<210> SEQ ID NO 1
<211> LENGTH: 21
<212> TYPE: RNA
<213> ORGANISM: Artificial Sequence
<220> FEATURE:
<223> OTHER INFORMATION: synthetic RNA oligonucleotide; cf. page 12, 30,
      32, 33, 34, 35, 36

<400> SEQUENCE: 1
aguguuaucu uguauggggg g                                              21

<210> SEQ ID NO 2
<211> LENGTH: 23
<212> TYPE: RNA
<213> ORGANISM: Artificial Sequence
<220> FEATURE:
<223> OTHER INFORMATION: synthetic RNA oligonucleotide; cf. page 30
```

<400> SEQUENCE: 2
cauuuccgau aaggcuuggg ggg                                              23

<210> SEQ ID NO 3
<211> LENGTH: 25
<212> TYPE: RNA
<213> ORGANISM: Artificial Sequence
<220> FEATURE:
<223> OTHER INFORMATION: synthetic siRNA sense strand; cf. page 31

<400> SEQUENCE: 3
cccaaauuac guguacuacg ggggg                                            25

<210> SEQ ID NO 4
<211> LENGTH: 19
<212> TYPE: RNA
<213> ORGANISM: Artificial Sequence
<220> FEATURE:
<223> OTHER INFORMATION: synthetic siRNA antisense strand; cf. page 31

<400> SEQUENCE: 4
guaguacacg uaauuggg                                                    19

<210> SEQ ID NO 5
<211> LENGTH: 818
<212> TYPE: RNA
<213> ORGANISM: Homo sapiens

<400> SEQUENCE: 5
auccucgugg gcccugaccu ucucucugag agccgggcag aggcuccgga gccaugcagg       60
ccgaaggccg gggcacaggg gguucgacgg gcgaugcuga uggcccagga ggcccuggca     120
uuccugaugg cccagggggc aaugcuggcg gcccaggaga ggcgggugcc acgggcggca     180
gagucccccg gggcgcaggg gcagcaaggg ccucggggcc gggaggaggc gccccgcggg     240
guccgcaugg cggcgcggcu ucagggcuga auggaugcug cagaugcggg gccaggggc      300 cggagagccg ccugcuugag uucuaccucg ccaugccuuu cgcgacaccc auggaagcag     360
agcuggcccg caggagccug gcccaggaug ccccaccgcu ucccgugcca ggggugcuuc     420
ugaaggaguu cacugugucc ggcaacauac ugacuauccg acugacugcu gcagaccacc     480
gccaacugca gcucuccauc agcuccuguc ccagcagcu uucccuguug auguggauca     540
cgcagugcuu ucugcccgug uuuuuggcuc agccucccuc agggcagagg cgcuaagccc     600
agccuggcgc cccuuccuag gucaugcccuc ucccccuagg gaauggucccc agcacgagug    660 gccaguucau uggggggcc ugauuguuug ucgcuggagg aggacggcuu acauguuugu      720
uucuguagaa aauaaaacug agcuacgaaa aaaaaaaaaa aaaaaaaaaa aaaaaaaaa      780 aaaaaaaaaa aaaaaaaaa aaaaaaaaa aaggggg                                818

<210> SEQ ID NO 6
<211> LENGTH: 15
<212> TYPE: RNA
<213> ORGANISM: Artificial Sequence
<220> FEATURE:
<223> OTHER INFORMATION: synthetic RNA oligonucleotide; cf. page 34

<400> SEQUENCE: 6
aguguuaucu uguau                                                       15

<210> SEQ ID NO 7

```
<211> LENGTH: 17
<212> TYPE: RNA
<213> ORGANISM: Artificial Sequence
<220> FEATURE:
<223> OTHER INFORMATION: synthetic RNA oligonucleotide; cf. page 34

<400> SEQUENCE: 7
aguguuaucu uguaugg                                                    17

<210> SEQ ID NO 8
<211> LENGTH: 19
<212> TYPE: RNA
<213> ORGANISM: Artificial Sequence
<220> FEATURE:
<223> OTHER INFORMATION: synthetic RNA oligonucleotide; cf. page 34

<400> SEQUENCE: 8
aguguuaucu uguaugggg                                                  19

<210> SEQ ID NO 9
<211> LENGTH: 21
<212> TYPE: RNA
<213> ORGANISM: Artificial Sequence
<220> FEATURE:
<223> OTHER INFORMATION: synthetic RNA oligonucleotide; cf. page 34

<400> SEQUENCE: 9
aguguuaucu uguauaaaaa a                                               21

<210> SEQ ID NO 10
<211> LENGTH: 21
<212> TYPE: RNA
<213> ORGANISM: Artificial Sequence
<220> FEATURE:
<223> OTHER INFORMATION: synthetic RNA oligonucleotide; cf. page 34

<400> SEQUENCE: 10
aguguuaucu uguauccccc c                                               21

<210> SEQ ID NO 11
<211> LENGTH: 21
<212> TYPE: RNA
<213> ORGANISM: Artificial Sequence
<220> FEATURE:
<223> OTHER INFORMATION: synthetic RNA oligonucleotide; cf. page 34

<400> SEQUENCE: 11
aguguuaucu uguauuuuuu u                                               21

<210> SEQ ID NO 12
<211> LENGTH: 21
<212> TYPE: RNA
<213> ORGANISM: Artificial Sequence
<220> FEATURE:
<223> OTHER INFORMATION: synthetic RNA oligonucleotide; cf. page 34

<400> SEQUENCE: 12
aguguuaggg gggucuugua u                                               21

<210> SEQ ID NO 13
<211> LENGTH: 21
<212> TYPE: RNA
<213> ORGANISM: Artificial Sequence
<220> FEATURE:
<223> OTHER INFORMATION: synthetic RNA oligonucleotide; cf. page 34

<400> SEQUENCE: 13
```

```
gggggggagug uuaucuugua u                                    21

<210> SEQ ID NO 14
<211> LENGTH: 21
<212> TYPE: RNA
<213> ORGANISM: Artificial Sequence
<220> FEATURE:
<223> OTHER INFORMATION: synthetic RNA oligonucleotide; cf. page 35

<400> SEQUENCE: 14
aguguuaucu uguauggaag g                                     21

<210> SEQ ID NO 15
<211> LENGTH: 18
<212> TYPE: RNA
<213> ORGANISM: Artificial Sequence
<220> FEATURE:
<223> OTHER INFORMATION: synthetic RNA oligonucleotide; cf. page 37

<400> SEQUENCE: 15
auauucuugu auggggg                                          18
```